(12) United States Patent
Fukunaga et al.

(10) Patent No.: US 7,717,109 B2
(45) Date of Patent: May 18, 2010

(54) BREATHING SYSTEMS WITH POST-INSPIRATORY VALVE FRESH GAS FLOW INPUT, COMPONENTS FOR IMPLEMENTING SAME, AND METHODS OF USE

(75) Inventors: Atsuo F. Fukunaga, Palos Verdes Peninsula, CA (US); Blanca M. Fukunaga, Palos Verdes Peninsula, CA (US); Alex S. Fukunaga, Palos Verdes Peninsula, CA (US)

(73) Assignee: F-Concepts LLC, Rancho Palos Verdes, CA (US)

( * ) Notice: Subject to any disclaimer, the term of this patent is extended or adjusted under 35 U.S.C. 154(b) by 922 days.

(21) Appl. No.: 10/390,070

(22) Filed: Mar. 14, 2003

(65) Prior Publication Data

US 2003/0183232 A1    Oct. 2, 2003

Related U.S. Application Data

(63) Continuation-in-part of application No. 10/254,700, filed on Sep. 24, 2002, now Pat. No. 6,874,500.

(60) Provisional application No. 60/340,206, filed on Dec. 12, 2001, provisional application No. 60/324,554, filed on Sep. 24, 2001.

(51) Int. Cl.
*A62B 7/00* (2006.01)

(52) U.S. Cl. .............................. 128/204.18; 128/203.26; 128/204.21; 128/205.24

(58) Field of Classification Search ............ 128/204.18, 128/204.21, 204.22, 205.18, 205.24, 203.26
See application file for complete search history.

(56) References Cited

U.S. PATENT DOCUMENTS

| 3,556,097 | A | 1/1971 | Wallace |
| 3,713,440 | A | 1/1973 | Nicholes |
| 3,856,051 | A | 12/1974 | Bain |
| 4,007,737 | A | 2/1977 | Paluch |
| 4,148,732 | A | 4/1979 | Burrow et al. |
| 4,188,946 | A | 2/1980 | Watson et al. |
| 4,232,667 | A | 11/1980 | Chalon et al. |
| 4,265,235 | A | 5/1981 | Fukunaga |

(Continued)

FOREIGN PATENT DOCUMENTS

AT                93941              8/1923

(Continued)

OTHER PUBLICATIONS

Andrews, J. Jeffrey, *Inhaled Anesthetic Delivery Systems*, Anesthesia, Fourth Edition, pp. 185; and 203-207.

(Continued)

*Primary Examiner*—Darwin P Erezo
(74) *Attorney, Agent, or Firm*—Daniel Schein, Esq.

(57) ABSTRACT

A system for providing anesthesia or assisted ventilation that has a post-inspiratory valve fresh gas flow input is disclosed. In a preferred embodiment, a fresh gas flow diverter valve is provided to permit an operator to provide fresh gas flow proximally or distally of the inspiratory valve. Also disclosed is an adaptor and other breathing circuit components for forming a system of the present invention. A method of providing anesthesia or assisted ventilation using low flow fresh gas is disclosed.

8 Claims, 16 Drawing Sheets

U.S. PATENT DOCUMENTS

| | | | |
|---|---|---|---|
| 4,269,194 A | 5/1981 | Rayburn et al. | |
| 4,318,398 A | 3/1982 | Oetjen et al. | 128/201.13 |
| 4,367,769 A | 1/1983 | Bain | 138/114 |
| 4,391,271 A | 7/1983 | Blanco | |
| 4,453,543 A | 6/1984 | Kohnke et al. | 128/205.12 |
| 4,462,397 A | 7/1984 | Suzuki | |
| 4,463,755 A | 8/1984 | Suzuki | |
| 4,596,246 A | 6/1986 | Lyall | |
| 4,621,634 A | 11/1986 | Nowacki et al. | |
| 4,637,384 A | 1/1987 | Schroeder | |
| 4,657,532 A | 4/1987 | Osterholm | |
| 4,676,239 A | 6/1987 | Humphrey | 128/203.12 |
| 4,809,706 A | 3/1989 | Watson et al. | |
| 4,938,210 A | 7/1990 | Shene | 128/203.12 |
| 4,967,744 A | 11/1990 | Chua | 128/204.18 |
| 5,002,050 A | 3/1991 | McGiinnis | 128/203.11 |
| 5,088,486 A | 2/1992 | Jinotti | |
| 5,121,746 A | 6/1992 | Sikora | 128/203.12 |
| 5,140,983 A | 8/1992 | Jinotti | |
| 5,195,527 A | 3/1993 | Hicks | |
| 5,230,727 A | 7/1993 | Pound et al. | |
| 5,284,160 A | 2/1994 | Dryden | |
| 5,320,093 A | 6/1994 | Raemer | |
| 5,377,670 A | 1/1995 | Smith | 128/204.17 |
| 5,404,873 A | 4/1995 | Leagre et al. | |
| 5,546,930 A | 8/1996 | Wikefeldt | |
| 5,623,922 A | 4/1997 | Smith | 128/204.18 |
| 5,715,815 A | 2/1998 | Lorenzen et al. | |
| 5,722,391 A | 3/1998 | Rosenkoetter et al. | |
| 5,778,872 A | 7/1998 | Fukunaga et al. | 128/202.27 |
| 5,823,184 A | 10/1998 | Gross | 128/294.18 |
| 5,901,705 A | 5/1999 | Leagre | |
| 5,983,891 A | 11/1999 | Fukunaga | 128/200.24 |
| 5,983,894 A | 11/1999 | Fukunaga et al. | 128/205.29 |
| 5,983,896 A | 11/1999 | Fukunaga et al. | 128/207.14 |
| 6,003,511 A | 12/1999 | Fukunaga et al. | 128/202.27 |
| 6,354,292 B1 | 3/2002 | Fisher | |
| 6,408,848 B1 * | 6/2002 | Feldman et al. | 128/205.14 |
| 6,874,500 B2 * | 4/2005 | Fukunaga et al. | 128/204.18 |
| 7,261,105 B2 * | 8/2007 | Fukunaga et al. | 128/204.18 |
| 7,275,541 B2 * | 10/2007 | Fukunaga et al. | 128/204.18 |
| 2005/0150505 A1 | 7/2005 | Burrow et al. | 128/911 |

FOREIGN PATENT DOCUMENTS

| | | |
|---|---|---|
| EP | 0 462 412 A2 | 12/1991 |
| EP | 0 982 044 A2 | 8/1999 |
| EP | 0 982 044 A3 | 8/1999 |
| EP | 01 11 7999 | 12/2001 |
| EP | 05 07 7222 | 3/2006 |
| EP | 03798654.4-2310 | 5/2006 |
| GB | 1 270 946 | 4/1972 |
| WO | WO 82/00766 | 3/1982 |
| WO | WO 85/05277 | 12/1985 |
| WO | WO 91/19527 | 12/1991 |
| WO | WO 98/26710 | 12/1996 |
| WO | WO 01/08736 A1 | 2/2001 |
| WO | WO 03/026721 | 4/2003 |

OTHER PUBLICATIONS

Byrick, R.J., et al., "Rebreathing and Co-Axial Circuits: A Comparison of the Bain and Mera F", *Canad. Anaesth. Soc. J.*, vol. 28, pp. 321-328 (1981).

Okazaki, et al., "Effect of Carbon Dioxide (Hypocapnia and Hypercapnia) on Internal Mammary-Coronary Arterial Bypass Graft Blood Flow and Regional Myocardial Oxygen Tension in the Dog", *Anesthesiology*, vol. 81, No. 3A, A717 (1994).

Paterson, J.G., et al., "A Hazard Associated with Improper Connection of the Bain Breathing Circuit", *Canad. Anaesth. Soc. J.*, vol. 22, pp. 373-377 (1975).

Pilbeam, Susan P., *Mechanical Ventilation, $2^{nd}$ Ed., Mosby Year Book*, St. Louis, Missouri, pp. 285-286 (1992).

Pontoppidan, H., et al., "Acute Respiratory Failure in the Adult", *The New England Journal of Medicine*, vol. 287, pp. 743-752 (1972).

Robinson, S., et al., "Safety Check for the CPRAM Circuit", *Anesthesiology*, vol. 59, pp. 488-489 (1983).

Scott, P.V., et al., "Variable Apparatus Deadspace", *Anaesthesia*, vol. 46, No. 9, pp. 1047-1049 (1991).

Shapiro, B.A., et al., "Clinical Application of Respiratory Care", *Yearbook Medical Publishers, Inc.*, pp. 351-352 ("Principles of Ventilator Maintenance") (1979).

Stoyka, W., "The Reliability and Usefulness of the Suwa Nomogram in Patients in Respiratory Failure", *The Canadian Anaesthetists' Society Journal*, pp. 119-128 (1970).

Suwa, K., et al., "Change in $Pa_{co2}$ with mechanical dead space during artificial ventilation", *Journal of Applied Physiology*, vol. 24, pp. 556-561 (1968).

Advertisement of the CPRAM™ Coaxial Circuits by Dryden Corporation, Indianapolis, Indiana.

Advertisement of the ACE Breathing Circuit™ by Meridian Medical Systems, Inc., Indianapolis, Indiana.

Fletcher, R., Scott, P. V., Jones, R.P., "The variable deadspace is not necessary," Correspondence reported in *Anaesthesia*, vol. 47, No. 7, pp. 623-624 (1992).

Nunn, J.F., *Applied Respiratory Physiology with special reference to anaesthesia*, London, Butterworths, 1971.

Eger, E.I. II, "Anesthetic Systems: Construction and Function", *Anesthetic Uptake and Action*, Baltimore, Williams & Wilkins, 1974 pp. 206-227 (1974).

Eger, E.I. II et al., "The Effect of Inflow, Overflow and Valve Placement on Economy of the Circle System", *Anesthesiology*, pp. 29:93-100 (1968).

Mentell, O. et al., "A new hybrid anaesthetic circuit for a low-flow rebreathing technique", *Acta Anaesthesiologica Scandinavica*, pp. 38:840-844 (1994).

Johansson, A. et al., "The Quotient End-Tidal/Inspired Concentration of Sevoflurane in a Low-Flow System", *Journal of Clinical Anesthesia*, 14:267-270 (2002).

Coetzee, J.F. et al., "Fresh gas flow is not the only determinant of volatile agent consumption: a multi-centre study of low-flow anaesthesia", *British Journal of Anaesthesia*, 88:46-55 (2002).

* cited by examiner

BREATHING SYSTEMS WITH POST-INSPIRATORY VALVE FRESH GAS FLOW INPUT, COMPONENTS FOR IMPLEMENTING SAME, AND METHODS OF USE

PRIORITY

This application is a continuation-in-part of U.S. non-provisional patent application Ser. No. 10/254,700, filed Sep. 24, 2002 now U.S. Pat. No. 6,874,500, which claims priority of U.S. provisional patent application Ser. No. 60/340,206, filed Dec. 12, 2001 and U.S. provisional patent application Ser. No. 60/324,554, filed Sep. 24, 2001, all of which are specifically incorporated by reference as if reproduced in full below.

FIELD OF THE INVENTION

This invention relates to devices for use in providing anesthesia and/or assisted and artificial ventilation to patients, and more particularly relates to ventilation systems that optimize utilization of fresh gases (e.g., anesthetic agents and oxygen) during provision of anesthesia and/or assisted and artificial ventilation, components for forming same, and methods of use. These inventions lead to substantial fresh gas savings.

BACKGROUND OF THE INVENTION

Breathing Circuits

Commonly used circuits for use in assisted ventilation systems have two limbs (e.g., two independent tubes). The ends of the tubes in a breathing circuit are generally held in spaced relationship by a connector located at the patient or distal end of the circuit. The connector can place the distal (i.e., patient) ends of the tubes in a fixed parallel relationship, or the connector can be a Y-piece with the two tubes converging at an angle.

Breathing circuits may be classified based on how carbon dioxide is eliminated. Carbon dioxide can be eliminated by "washout", which is dependent on the fresh gas inflow (i.e., $CO_2$ absorption is not required, e.g., in a Mapleson type circuit), or by using a $CO_2$ absorber such as soda lime and the like (i.e., as in a circle circuit). Thus, breathing circuits in anesthesia are generally provided as circle circuits (for $CO_2$ absorption systems) or Mapleson type circuits.

Circle $CO_2$ Absorption and Mapleson Type Breathing Systems

In a "circle system," a one-way valve permits gases to flow to a patient from a machine through a first or inspiratory conduit, while another one-way valve permits partial recirculation of the gases by causing expired gases to flow from the patient through a second or expiratory conduit to a "recirculation module" (also called a "scrubber circuit," "scrubber module," or similar term). The recirculation module generally comprises a carbon dioxide absorber to eliminate the carbon dioxide in expired gases to produce "scrubbed gases." The scrubbed gases are then combined with the fresh gases coming from the anesthesia machine, and the mixed gases are referred to herein as "refreshed gases." Some or all of the refreshed gases can be rebreathed by the patient.

Excess gases are directed to an exhaust conduit and/or scavenger. Thus, new fresh gases are combined with scrubbed gases at the scrubber circuit, and are delivered as refreshed gases to the first or inspiratory conduit, while expired gases are carried by a second or expiratory conduit to a "scrubber circuit" for recirculation and/or exhaust. Generally, circle systems have an inspiratory port operatively connected in line with the one-way inspiratory valve, and an expiratory port operatively connected in line with the one-way expiratory valve. In use, a patient inspiratory conduit or lumen is operatively connected to the inspiratory port and a patient expiratory conduit is operatively connected to the expiratory port to form a circuit.

In Mapleson A-F type circuits, fresh gas is delivered into a common breathing tube by a fresh gas delivery/supply tube, wherein the breathing tube acts to provide gases to the patient and receive expired gases therefrom (since the common breathing tube handles both inspiratory and expiratory gases, it is also referred to as a rebreathing tube or conduit). Generally, the diameter of the fresh gas supply tube is small, thereby limiting its function to being a fresh gas delivery or supply conduit rather than an inspiratory tube (i.e., an inspiratory tube is a tube from which a patient directly inspires as in the circle system). A Mapleson D type circuit, the most commonly used circuit among the Mapleson circuits, does not use valves, therefore, the flow of fresh gases required must be sufficiently high to minimize $CO_2$ rebreathing. During inspiration, the patient will inhale fresh gases from the fresh gas delivery/supply tube inlet and gases from the common breathing tube, which may be a mixture of fresh gas and expired alveolar gases. High fresh gas flow will flush the breathing tube, pushing the expired alveolar gases out of the circuit. A more detailed explanation of the operation of a typical Mapleson D and circle system follows.

Operation of Mapleson D System and Circle $CO_2$ Absorption System

With reference to FIGS. 1A-D, drawing 1A illustrates a schematic diagram of a prior art Mapleson D system, in which the fresh gas flow ("FGF") 1 is provided via fresh gas delivery tube 2 (shown in schematic form only) to a distal fitting 3. There are no valves in this system. The operation of the system is better understood by reference to the numbered arrows and part numbers in the Figures. During inspiration, gas to lungs 4 flows simultaneously from fresh gas flow inlet 1 and bag 7 via flow path a, 1→2→3→4, and flow path b, 7→6→5→4 (flow paths are also provided in the keys below FIGS. 1A and 1C). During expiration, gases flow from lungs 4 to waste gas outlet 8 via flow path a', 1→2→3→5, and flow path b', 4→5→6→7→8.

Drawing 1B illustrates a Bain circuit used as a Mapleson D system (see U.S. Pat. No. 3,856,051). A key feature of the Bain is that the fresh gas delivery tube 2 is inserted in the proximal terminal at the proximal end of the circuit and the tube extended through rebreathing tube 5 to have its distal end 3 at the distal end of the circuit. Note that the Mapleson D system provides the fresh gases at the distal end of the circuit, but at high flow, and does not use valves.

Drawing 1C illustrates a circle $CO_2$ absorption system, which has a $CO_2$ absorber 12, check valves (i.e., unidirectional valves) 4 and 9, as well as an inspiratory conduit 5 and an expiratory conduit 8 that meet at a distal fitting 6. During inspiration, gas to lungs 7 flows simultaneously from fresh gas flow source 1 and bag 10 via flow paths c, 1→2→3→4→5→6→7, and flow path d, 10→12→4→5→6→7. During expiration, gases flow from lungs 7 to waste gas outlet 11 via flow path c' 1→2→3→12, and flow path d', 7→6→8→9→10→11. Valve 4 is an inspiratory valve and valve 9 is an expiratory valve. Note that fresh gas flow inlet 3 is proximal of the inspiratory valve (i.e., is located "pre-inspiratory valve").

It is important to note that in the prior art circle system, fresh gases are combined with recirculated scrubbed gases near or at the $CO_2$ absorber prior to (i.e., proximally of) the one-way inspiratory valve, and carried in an inspiratory conduit 5 to the patient. The gases in a circle system thus flow in one direction in a circuitous path from a machine to a patient via an inspiratory conduit, from a patient through an expiratory conduit to the machine, with some gases then passing through a scrubber to the inspiratory conduit (hence, while a rebreathing tube is used in a Mapleson type circuit, such a circuit is referred to as a non-rebreathing circuit because the high fresh gas flows provided wash out the exhaled gases, thereby avoiding carbon dioxide rebreathing). Considerable effort is required to modify an assisted ventilation system from a circle arrangement to a Mapleson type non-rebreathing arrangement. U.S. Pat. No. 4,596,246 discloses a method and apparatus for facilitating the conversion between a circle and a non-rebreathing system (the "Lyall system"). An adaptor and fittings are taught to permit more ready exchange between a Bain type non-rebreathing configuration and a circle configuration. However, both configurations in the Lyall system work in the traditional manner, i.e., expired gas is not recycled to the patient in the Bain configuration.

The tubing and fittings for connecting a patient to the inspiratory and expiratory ports of an assisted ventilation system in a circle system are often referred to as "a circuit." Likewise, the fresh gas tube, breathing tube, and proximal and distal fittings used in a Mapleson type system are referred to as "a circuit." When the two tubes are in substantially close-spaced parallel relationship, such that they essentially form one multilumen limb, the circuit is referred to a unilimb circuit. For example, the Bain circuit is considered to be a unilimb circuit since the fresh gas tube is inside of the breathing tube. Other unilimb circuits include, but are not limited to, coaxial conduits, side-by-side conduits which are closely spaced or connected to each other, or conduits that share a common wall.

The Universal F® Circuit

With reference to U.S. Pat. No. 4,265,235, to Fukunaga, a unilimb device of universal application for use in different types of breathing systems is described which provides many advantages over prior systems. The Fukunaga device, sold as the Universal F® by King Systems Corporation of Noblesville, Ind., U.S.A., utilizes a space saving co-axial, or tube within a tube, design to provide inspiratory gases and remove expiratory gases. Numerous advantages flow from this arrangement, such as a reduction in the size of the breathing apparatus connected to a patient. Further, the device acts as an artificial nose since the expired gases warm and maintain humidity of the inspired gases as the two opposing flows are countercurrent in the unilimb device. Unlike the Bain Circuit, the coaxial tubes provide flow paths of sufficient cross-sectional area to use the Universal F® circuit in a circle system.

Universal F2® Technology

With reference to U.S. Pat. No. 5,778,872, to Fukunaga et al., unilimb multi-lumen circuits are disclosed and embodiments thereof are sold as the F2™ or Universal F2® by King Systems Corporation of Noblesville, Ind., U.S.A. The F2™ inventions have revolutionized artificial ventilation systems and methods of providing assisted ventilation and anesthesia. The F2™ system provides for safe and ready attachment and detachment of multilumen (e.g., co-axial) system components from the proximal terminal. This permits more efficient placement and utilization of other breathing circuit components, improves system performance, and yet reduces medical waste and costs. In general, the Universal F® and the F2™ are used in a circle system configuration with a carbon dioxide absorber. For more information about the F2™ technology, one may contact King Systems Corporation.

Drawing 1D illustrates a circle $CO_2$ absorption system, which uses either a Universal F® circuit or Universal F2® circuit (the latter will use an F2™-type proximal terminal and detachable proximal fitting). Inspiratory conduit 5 is coaxial within expiratory conduit 8 distal of the proximal terminal.

For further information on breathing systems, and anesthetic and assisted ventilation techniques, see U.S. Pat. Nos. 3,556,097, 3,856,051, 4,007,737, 4,188,946, 4,265,235, 4,463,755, 4,232,667, 4,596,246, 5,121,746, 5,284,160, 5,778,872, Austrian Patent No. 93,941, British Patent 1,270, 946, Dorsch, J. A., and Dorsch, S. E., *Understanding Anesthesia Equipment: Construction, Care And Complications*, Williams & Wilkins Co., Baltimore (1974), and Andrews, J. J., "Inhaled Anesthetic Delivery Systems," in *Anesthesia*, $4^{th}$ Ed. Miller, Ronald, M. D., Editor, Churchill Livingstone, Inc., N.Y. (1986). The text of all documents referenced herein, including documents referenced within referenced documents, is hereby incorporated by reference as if same were reproduced in full below.

More Cost Effective Anesthesia and Assisted Ventilation Systems are Needed

The Universal F® and Universal F2® technologies described above have led to a substantial reduction in medical wastes, yet provide for improved ventilation systems and health benefits to patients. These enhancements will be further improved with the F3™ technologies described in copending U.S. patent application Ser. No. 10/254,700.

However, it is desired to further enhance patient care while reducing the use and/or waste of respiratory gases. Low fresh gas flow anesthesia techniques (also referred to as "low FGF" or "low flow" anesthesia or similar terms) have considerable advantages over high flow anesthesia methods. They reduce the amount of wasted anesthetic gases and healthcare costs. Moreover, such methods maintain better humidification and improve modulation of the temperature of inhaled gases. Low flow methods also minimize the amount of gas released from the system to the environment, which reduces operating room pollution, thus providing a safer working environment. However, low flow techniques, even with the circle system, have not been widely adapted due to a variety of concerns.

Because Mapleson D type systems require high fresh gas flows ("high FGF"), the circle system is the most widely accepted system. A major concern of low flow techniques in anesthesia is the uncertainty and unpredictability of the inspired and alveolar concentration of anesthetics provided to the patient. Anesthetics must be administered in sufficient dosages to achieve desired anesthetic endpoints (e.g., avoiding patient awareness during surgery without overdosing). It is believed that in low flow anesthesia with the circle system, the anesthetic concentration of the refreshed gases decreases progressively from the initial fresh gas concentration (concentration at the vaporizer) in the process of re-circulation. Such a decrease may be due to anesthetic uptake and dilution by the expired gases and/or scrubbed gases, leakage, and adsorption and/or absorption by plastic, rubber, and other materials in the system. With high fresh gas flows, the inspired (anesthetic) gas concentration (FI or $F_I$) can be assumed to be equivalent to the delivered gas concentration (FD or $F_D$=vaporizer setting concentration). Such an assumption cannot be made with low flow anesthesia.

With prior art technologies, lowering the FGF results in a gradually increasing gradient (difference) between the delivered gas concentration (FD) and the patient's inspired gas (FI), which is in part due to the increasing dilution of the fresh gas with the scrubbed gases within the system. For example, during low FGF of less than 3 L/min, there are significant discrepancies (over 20%) between the inspired gas concentration and the delivered gas concentration (e.g., the volatile anesthetic vaporizer setting concentration). This may result in under-anesthetized patients.

A further concern with low flow anesthesia using the circle system is the interaction of volatile anesthetics with the carbon dioxide absorber (e.g., soda lime), which has been recently reported as producing toxic substances. This concern includes the formation of carbon monoxide and Compound A during degradation of volatile anesthetics by soda lime. For example, CO has been found in anesthetics, including halothane, enflurane, isoflurane and desflurane circle systems. Moreover, in the case of sevoflurane, it is known that sevoflurane is degraded in the presence of soda lime to olefin and Compound A, which has been reported to have nephrotoxic potential. Therefore, in view of such concerns, low flow anesthesia has not been recommended unless constant flow adjustments and vaporizer setting adjustments are made during anesthesia and by very careful monitoring of the inspiratory and the end-tidal gas concentrations.

Despite potential benefits provided by low flow anesthesia techniques, higher flow methods and systems are still being used. Therefore, there is a need to improve these systems and methods to make them simple, safe and commercially practical.

SUMMARY OF THE INVENTION

The present invention is directed to new breathing systems and circuits with post-inspiratory valve fresh gas flow input, components for implementing same, and methods of optimizing utilization of fresh gases during artificial or assisted ventilation and/or anesthesia using such systems.

A preferred breathing system includes a new scrubber module, referred to herein as the "F-scrubber" (or F-scrubber™), having a scrubber housing that comprises an inspiratory valve, an expiratory valve, and a scrubber chamber with a scrubber fresh gas input. In a first embodiment, the F-scrubber includes a diverter mechanism that can divert fresh gas flow from the scrubber fresh gas input to a point distal of the inspiratory valve in the inspiratory flow path. In a second embodiment, the F-scrubber includes a post-inspiratory valve fresh gas flow input operatively connected in the inspiratory path at a point distal to the inspiratory valve. In a third embodiment, the F-scrubber includes both the diverter and the post-inspiratory valve fresh gas flow input.

New F3™ circuits are also provided having at least two inlet ports, one for scrubbed gases ("scrubbed gas port") and another for fresh gases ("fresh gas port"), and also having a port for expiratory gases to be directed to the machine ("proximal expiratory port"). The circuits also include respiratory conduits with a port to provide respiratory gases to a patient ("respiratory port"), and a port to receive expiratory gases from the patient ("distal expiratory port"). In a preferred system embodiment, the first embodiment of the scrubber module described above incorporates a new F3™ circuit, wherein the new circuit provides a post-inspiratory valve fresh gas flow input.

In an embodiment, a Mapleson D type system is modified and combined with a modified $CO_2$ absorption circle system to produce an efficient gas-saving system (also referred to herein as a "COMBO" or "F-COMBO" system), wherein the system is capable of optimizing the utilization of anesthetic gases in a safe and predictable manner. By providing undiluted fresh gases at the patient side (i.e., distal end of the circuit) and circulating the expired gases through a scrubber circuit having a carbon dioxide absorber, the system provides assurance that the patient receives more accurate fresh gas concentrations (i.e., close to the anesthesia machine flow meter's oxygen and nitrous oxide concentrations and the volatile anesthetic vaporizer's concentration setting). In addition, recirculating the expired gases allows re-use of the gases after $CO_2$ elimination. As a result, utilization of fresh gases is optimized. In a preferred embodiment, the COMBO systems use a unilimb multilumen breathing circuit wherein the dimensions of at least one of the conduits can be altered to adjust the volume in the rebreathing tube. This embodiment permits the amount of rebreathing to be titratable and predictably adjusted, and the same breathing conduit or circuit may be utilized universally in adult and pediatric cases. In this new COMBO, the rebreathing tube will be used to provide recirculated gases to patients, in contrast to prior art Mapleson type systems, in which the rebreathing tube did not supply recirculated gases (e.g., scrubbed gases) to the patient.

Another embodiment of the new breathing system with post-inspiratory valve fresh gas flow input is easy to use with conventional two-limb circuits, Universal F®, Universal F2®, and F3™ technologies. It is referred to herein as an F-conomy™ system due to its ability to economize on the use of respiratory and/or anesthetic gases. A typical F-conomy™ system has all of the traditional components of a circle system, including inspiratory and expiratory ports for connecting a scrubber module to corresponding conduits carrying gases to and from a patient respectively. A one-way valve operatively connected to the inspiratory gas port forms an inspiratory valve, which allows scrubbed gases to flow towards a patient from the assisted ventilation or anesthesia machine. A one-way valve is operatively connected to the expiratory gas port, forming an expiratory valve, which permits expiratory gases to flow only from the patient expiratory conduit to the machine. Embodiments of the F-conomy™ system incorporate the new F-scrubber described above. The system may include other components found in standard assisted ventilation and anesthesia machines.

In a preferred system embodiment, a first or distal fresh gas flow input port (also referred to as "post-inspiratory valve FGF input," "distal FGF input," "first FGF input," "low FGF input," or similar term) is provided distally of the inspiratory valve. A second or proximal fresh gas flow input ("proximal FGF input" or "second FGF input") is provided on the scrubber module (also referred to as a "pre-inspiratory valve FGF input," or "scrubber FGF input").

The F-conomy™ system preferably also includes a FGF diverter valve, which is operatively connected to the first fresh gas flow input distal of the inspiratory valve and operatively connected to the second FGF input on the scrubber module (the valve may also be referred to as an "F-diverter™," "F-converter" or similar term). In an embodiment, the F-diverter™ has at least two operating positions: a first position in which fresh gases are supplied only to the FGF input on the scrubber module (i.e., proximal of the inspiratory valve), and a second position in which fresh gas flow is directed only to a point in the inspiratory gas flow path that is distal of the inspiratory valve. In the second position, the F-diverter can also be readily connected to a nasal cannula to provide oxygen therapy in case of monitored anesthesia care (MAC) procedures, and may also be used in a COMBO™ system. The F-diverter can readily convert a circle system to a Mapleson type system like the Bain or Jackson-Rees systems. The F-diverter™ may also include an optional extra input for exclusive use in oxygen therapy. In an embodiment, the F-diverter may optionally seal the scrubber FGF input and divert FGF solely to a location in the inspiratory flow path distal of the inspiratory valve.

The F-conomy™ and COMBO™ systems provide new systems and methods of providing assisted ventilation and anesthesia. A simple and safe method of providing anesthesia or assisted ventilation at low FGF is made possible by the present inventions. In an embodiment, high fresh gas flow (high FGF) can be administered with the diverter valve in a position that directs the fresh gas flow into the scrubber module, and low fresh gas flow (low FGF) can be utilized by switching the diverter to a position that diverts the fresh gas flow to a point distally of the inspiratory valve for provision to a patient. The diverter has at least two FGF outputs and thus can switch FGF flow proximally and distally of the inspiratory valve, without requiring disconnection of the fresh gas flow lines connected to the diverter outputs. The patient may be human or non-human.

Existing scrubber modules and breathing systems can be modified by incorporation of a new diverter valve of the present invention and by the provision of a fresh gas flow adapter for FGF input placement distally of the inspiratory valve. The diverter valve and adapter may be provided together as a kit.

In an embodiment, a new FGF adapter (or "adaptor") has a rigid housing with an FGF conduit or nipple of a first diameter (i.e., minimum cross-sectional area) that is in fluid connection with and terminates in an inspiratory path conduit of a second diameter. The first diameter is preferably that conventionally used in tubing to provide FGF. Generally, the small first diameter limits the use of such tubing to serving only as a fresh gas delivery tube. The second diameter is sufficiently larger than the first diameter so that the inspiratory path conduit is not limited to serving only as a FGF tube. Hence, an inspiratory or rebreathing conduit should not be confused with a FGF conduit. For example, in a circle system, the patient directly inspires fresh and scrubbed gases from the inspiratory conduit.

In an embodiment, the fresh gas flow adapter is connectable to the inspiratory port on the distal end of a Universal F2® proximal terminal. In another embodiment, the features of the new adapter described above are incorporated into a new multilumen proximal terminal having (1) a machine or proximal expiratory port, (2) a scrubbed gas inspiratory port, (3) a fresh gas flow input port ("FGF port"), (4) a patient or distal inspiratory gas port, and (5) a patient or distal expiratory gas port. These new proximal terminals may be referred to as F3™ proximal terminals.

In another embodiment, the features of the new adapter described above are incorporated into a new multilumen proximal fitting for operative connection to a multilumen proximal terminal for a unilimb circuit, such as a multilumen Universal F2® proximal terminal. The new multilumen proximal fitting provides for fresh gas flow input into the inspiratory gas flow path distally of the inspiratory valve. These new proximal fittings may be referred to herein as F3™ proximal fittings.

The new FGF adapters, proximal terminals, and proximal fittings of the present inventions may also be modified to include filter means in the inspiratory and/or expiratory conduits (or rebreathing conduit as the case may be) using appropriate dimensional adjustments in the portions of the conduits containing the filter means to accommodate the filters and maintain desired flow.

Also disclosed is a new unitary circuit for rapid connection and disconnection by a user at the site of use to an assisted ventilation machine which provides for post-inspiratory valve fresh gas flow input.

The present inventions may be better understood by reference to the figures and further description below, which elaborates on the summary above and provides additional features. For the purposes of facilitating understanding of the invention, in the following figures certain fitting components are not shown and/or certain fitting components are shown in simplified form. For example, struts or flanges for spacing components from one another may not be shown, and wall thickness and relative tube diameters and lengths may not be to scale.

DESCRIPTION OF THE FIGURES

In FIGS. 2A-C the rebreathing tube volume may be adjusted.

FIG. 3C illustrates an F-scrubber scrubber embodiment connected to a FGF supply.

FURTHER DETAILED DESCRIPTION OF THE INVENTIONS

Definitions

Figure 1:
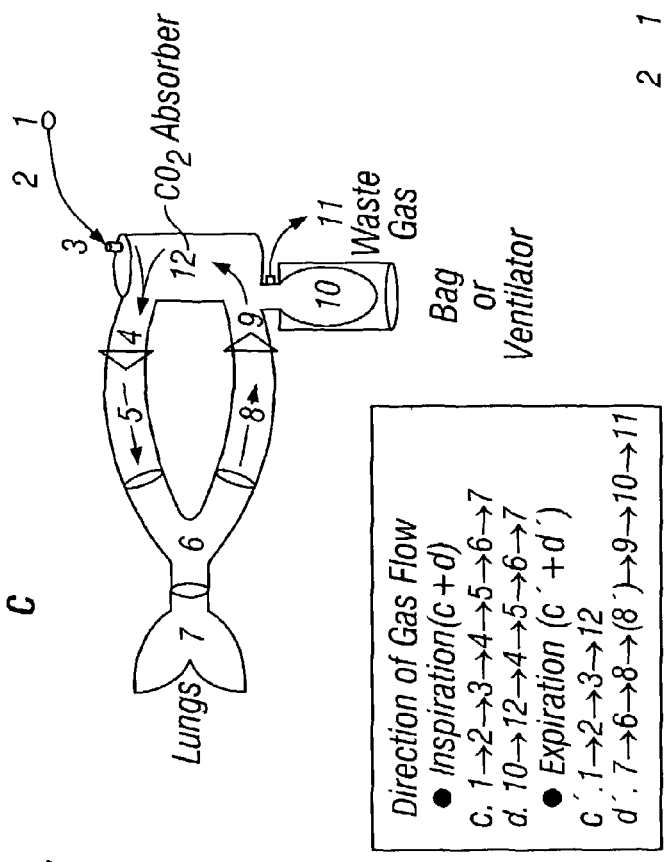
FIGS. 1A-D illustrate the operation of a prior art Mapleson D type system and prior art circle $CO_2$ absorption system.
Figure 1:
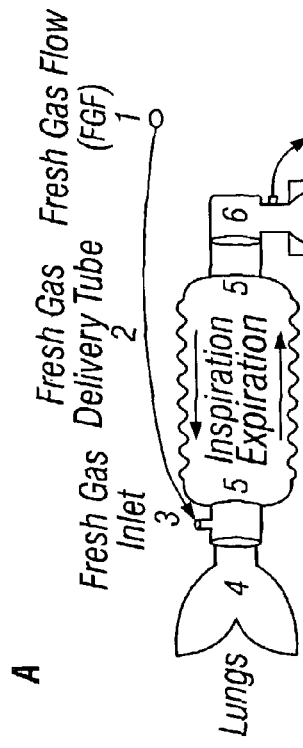
Figure 1:
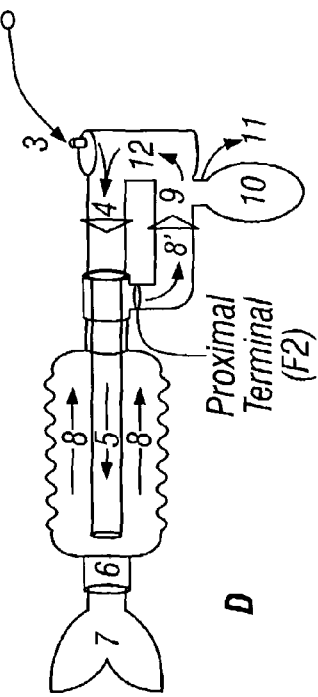
Figure 1:
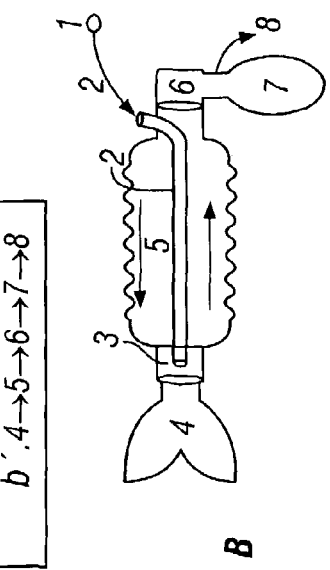

To facilitate further description of the prior art and the present invention, some terms are defined immediately below, as well as elsewhere in the specification. As used herein, the term "artificial or assisted ventilation" shall also incorporate "controlled and spontaneous ventilation" in both acute and chronic environments, including during anesthesia. Systems for use in anesthesia, artificial ventilation, or assisted ventilation may also be referred to as assisted ventilation systems. Fresh gases include but are not limited to gases such as oxygen and anesthetic agents such as nitrous oxide, halothane, enflurane, isoflurane, desflurane, and sevoflurane, that are generally provided by a flowmeter and vaporizer. FGF refers to fresh gas flow.

The end of a conduit directed toward a patient shall be referred to as the distal end, and the end of a conduit facing or connected to a source of inspiratory gases shall be referred to as the proximal end. Likewise, fittings and terminals or other devices at the distal end of the breathing circuit, e.g., connecting to or directed at the patient airway device (i.e., endotracheal tube, laryngeal mask, laryngeal tube, face mask etc.), will be referred to as distal fittings and terminals, and fittings and terminals or other devices at the proximal end of the breathing circuit will be referred to as proximal fittings and terminals. So, a distal adaptor or connector would be located at the distal or patient end of a circuit.

It is generally understood that a proximal terminal in a multilumen unilimb breathing circuit context is to be located at the machine end of the circuit and separates at least two independent flow paths formed by tubes that are in parallel closely-spaced or apposed relationship or that are coaxial in the circuit so that at least one flow path can be connected to a source of inspiratory gases while another flow path can be connected to an exhaust port that is spaced from the inspiratory gas port. A proximal terminal may also comprise a rigid housing that merges two independent flow paths into a common flow path, for example a Y-type fitting, preferably with a septum. For example, a proximal terminal may operatively connect a first flow path in the terminal to the expiratory port on an anesthesia machine, and operatively connect an independent second flow path in the terminal to the inspiratory port, wherein the first and second flow paths can be independently connected at the distal end of the proximal terminal to separate flexible tubes for carrying gases to and from a patient. The flexible tubes can be side by side, one within the other, closely spaced, or coaxial, so as to form a single multilumen limb. The proximal terminal of the present invention further comprises a port for receiving fresh gas flow from the assisted ventilation machine and merging the fresh gas flow with one of the independent flow paths in the terminal housing, and is referred to as an F3™ proximal terminal.

The use of a proximal fitting with a proximal terminal in a multilumen unilimb circuit is a new concept brought about by the Universal F2® inventions, which for the first time made it possible to readily connect and disconnect plural tubes to a proximal terminal for an assisted ventilation machine via a corresponding multilumen proximal fitting. In some embodiments of the present inventions, tubing may be directly bonded to a proximal terminal (which was done with prior art proximal terminals prior to the Universal F2® inventions, and hence required disposal or sterilization of the pre-F2™ proximal terminal and other circuit components as a unitary device). In other embodiments of the present invention, tubing may connect to a proximal fitting that can engage a corresponding port or ports on a proximal terminal. The proximal fitting may include filter means, or may engage a filter which in turn connects to a proximal terminal. In a preferred embodiment, a new multilumen proximal fitting is disclosed having a fresh gas flow input to one of the flow paths therein, and is referred to as an F3™ proximal fitting.

A proximal FGF adapter, or F3™ proximal adapter, is a new concept only made possible by the surprising discovery disclosed herein that low FGF can be safely provided with post-inspiratory valve FGF input, as previously there was no perceived need for FGF input at the proximal end of a breathing circuit distal of the inspiratory valve. The F3™ proximal adapter can be used in the proximal inspiratory limb of the COMBO circuit, as well as at any position distal of the inspiratory valve in a circle system where components can be readily attached and detached.

Herein, low fresh gas flow ("low FGF" or "low flow") is flow less than about 3 liters per minute (L/min) and high fresh gas flow ("high FGF" or "high flow") is above about 3 L/min. An inspiratory conduit (also referred to as inspiratory tube, lumen or pipe) is a conduit from which a patient inhales in a circle system. A rebreathing conduit is a conduit from which a patient inhales and exhales, as in a Mapleson type system; fresh gases are delivered to the rebreathing conduit from a fresh gas delivery or supply tube.

Gas Savings Systems

F3™ Combo System

With reference to FIG. 2, drawing 2A illustrates an assisted ventilation system of the present invention in schematic form that utilizes an embodiment of a new breathing circuit of the present invention.

To the right of dotted vertical line 20 is a traditional circle system, except for the provision of diverter 30. To the left of dotted line 20 is a Mapleson D type circuit. Hence this COMBO™ system combines the features of these prior circuits. The system may also be referred to, without limitation, as an F-COMBO, F-Combo, or COMBO, or F3 System.

Fresh gas flow from a source 1 (e.g., an anesthesia machine) passes via flow diverter 30 through fresh gas delivery tube 2 (shown in partial schematic form). Flow diverter 30 is provided for modifying a circle system having a scrubber fresh gas input port 15 in the scrubber circuit. The FGF input 15 is generally near or at the $CO_2$ absorber. The flow diverter closes off the fresh gas input port 15 on top of $CO_2$ absorber 12 so that fresh gases can be directly fed to the distal end 3 of the breathing conduit. In other words, FGF bypasses the scrubber module so it is not mixed with scrubbed gases. In this embodiment, FGF tube 2 includes an FGF conduit 56 that is, as with a Bain, rigidly bonded to proximal terminal 50, and also includes fresh gas flow lumen 58. Fresh gas flow can be continuously fed to the fitting 3 at the distal end of common inspiratory/expiratory conduit 5 (conduit 5 is also referred to as a rebreathing tube, common breathing conduit, or similar term). (In an embodiment, the diverter would not be needed if FGF port 15 was blocked or not present).

Expired gases in common breathing tube 5 enter the recirculation module at the expiratory port 22, while scrubbed gases from the recirculation module are provided to rebreathing tube 5 at inspiratory port 24. A first one-way valve 26 acts as an expiratory valve, permitting expiratory gases to enter the recirculation module from expiratory port 22, but not allowing for reverse flow. A second one-way valve 28 acts as an inspiratory valve, permitting scrubbed, fresh and/or refreshed gases from the recirculation module to flow to inspiratory port 24, but not allowing for reverse flow.

With reference to drawings 2A-C, unlike a Bain, the dimensions of rebreathing conduit 5 can be altered so that the tube volume and the concentration of its contents are altered; in this manner, the inspiratory gases can be adjusted for each patient, and rebreathing of scrubbed gases can be controlled (this is in contrast to the Lyall system). For example, tube 5 may be an ULTRA-FLEX® tube. Control can be achieved by adjusting the dimensions of tube 5, for example by axially adjusting the length of tube 5. Hence, titration of tube volumes and contents can be performed in response to inspired and/or end-tidal gas concentration data provided by the monitoring equipment. This feature facilitates low flow anesthesia with the COMBO.

Note that unlike the conventional circle system, in the new COMBO system of the present invention the fresh gases delivered directly from the anesthesia machine are not mixed or diluted at the machine/scrubber circuit end (i.e., proximally of the inspiratory valve). Because the fresh gas flow is delivered close to the patient, the inspired anesthetic concentrations ($F_I$) are almost equal to the delivered concentrations ($F_D$). Thus, the anesthetist can rely on the anesthetic concentrations reported by the flow meter and the vaporizer as indicative of the inspired concentrations. In contrast to the Mapleson D system, in the new system the expired gases are not all disposed of but some are reused as "refreshed gas," as expired gases pass through a scrubber module for recirculation as well as to equalize gas volume and pressure in the circuit (unlike the Lyall system). This new "F system" provides a surprising improvement in the control and quality of respiratory and anesthetic ventilation while avoiding waste of anesthetic gases.

Preferably, the volume of rebreathing tube 5 during use is adjusted to be larger than the tidal volume ($V_T$) to minimize mixing of the fresh gases with the "scrubbed gases". This allows optimal utilization of the fresh gases (anesthetic agents) as well as $O_2$ and $CO_2$ rebreathing control.

In a preferred embodiment, the length of the rebreathing tube may be variable for multiple usages. The same breathing system may be universally used, in an operating room, ICU, emergency room, respiratory care ward, in adult and pediatric cases, etc.

Drawing 2B illustrates a new proximal terminal 50 in schematic form that may be separately detached and connected to breathing conduit 5, and to fresh gas tube 2 and fresh gas flow lumen 58. Lumen 58 and conduit 5 may be connected to terminal 50 by a multilumen proximal fitting (not shown). Proximal terminal 50 is unique in that the FGF conduit 56 has a small diameter that is sufficient only for serving as a FGF delivery conduit, not as a breathing tube, and it likewise connects to a tube of similar cross-sectional area that may only serves as an FGF delivery tube. In this instance, the terminal does not connect independent lumens to an inspiratory port and an expiratory port on a breathing system as those ports are defined with respect to a circle system. Scrubbed and expired gases can pass through the common breathing lumen 54 without mixing with the fresh gas supply in FGF conduit 56 received at FGF input 52.

An additional flow splitting component 6 is also shown in schematic form, and is used in the traditional manner to combine flows in a first direction and divide flows in a second direction. Terminal 6 can be an F2® type proximal terminal or a Y adaptor. Expiratory gases are directed to expiratory port 22 and inspiratory "scrubbed gases" are received from inspiratory port 24. Fresh gases in FGF conduit 56 are directed to FGF lumen 58 when it is operatively connected thereto. The combination of readily attachable and detachable components facilitates independent sterilization or disposal.

For this embodiment and others inventions disclosed herein, the proximal and distal ends of the fittings, terminals and other components may be sized and uniquely shaped to match corresponding components, wherein users may only connect matching components. This may facilitate inventory control and produce a better fit between joined matching components.

In some instances, multiple components of this breathing circuit and others disclosed herein (e.g., tubes and fittings) are permanently bonded together, wherein substantial effort, potentially leading to breakage of the components, is required to separate the components. In other embodiments, multiple components of the breathing circuit can be integrally formed. Adaptors, fittings and terminals of the present invention comprise a rigid unitary housing that rigidly maintains the lumen shapes and configurations therein, whereas tubing to be connected thereto is generally flexible with thinner walls than the adaptors, fittings and terminals. Suitable materials for constructing the components of the present invention include but are not limited to those used and/or suitable for Universal F® and Universal F2® components. Standard tube dimensions and slip connectors as are known to those of skill in the art may be used (e.g., standards established by ISO).

Referring back to drawing 2A, the system components also preferably include a reservoir bag or ventilator device 10, waste gas outlet 11, which may be attached to a scavenger, $CO_2$ absorber 12, check valves 26 and 28 (inspiratory valve 28 and expiratory valve 26), inspiratory conduit 5', expiratory conduit 8', and a proximal terminal 6 that connects to proximal adapter 50. Proximal adaptor (or adapter) 50 is also referred to herein as a fresh gas flow adapter, and has a FGF input 52, and a FGF output 53 at opposite ends of an FGF conduit 56. Common (rebreathing) conduit 54 carries both scrubbed and expired gases in the system illustrated in FIG. 2A.

The operation of the system is better understood by reference to the numbered arrows and or part numbers. A Gas Flow key is provided in FIG. 2A. For example, in a preferred embodiment, during inspiration, gas to lungs 4 flows simultaneously from fresh gas flow source 1 and bag/ventilator 10 via inspiratory path a, 1→2→3→4, and inspiratory path b, 10→12→28→5'→6→5→3→4. During expiration, gases flow from lungs 4 to waste gas outlet 11 via expiratory path a', 1→2→3→5, and expiratory path b', 4→3→5→6→8'→26→10→11.

Diverter 30 is preferably included in the COMBO system, and preferably has a valve therein that permits a user to direct fresh gas flow to a fresh gas flow input 15 on scrubber 12 or to FGF input 52. This can be accomplished by manual movement of the F-diverter's lever, or by a suitable electromechanical valve mechanism in operative connection with the assisted ventilation or anesthesia machine controls and processor. In an embodiment, the F-diverter valve includes a cylindrical valve housing with a mating 3-way stop cock mounted therein, wherein the input and output conduits connect to the valve housing and can be aligned with lumens in the stop cock by rotation of the stop cock.

Figure 2A:
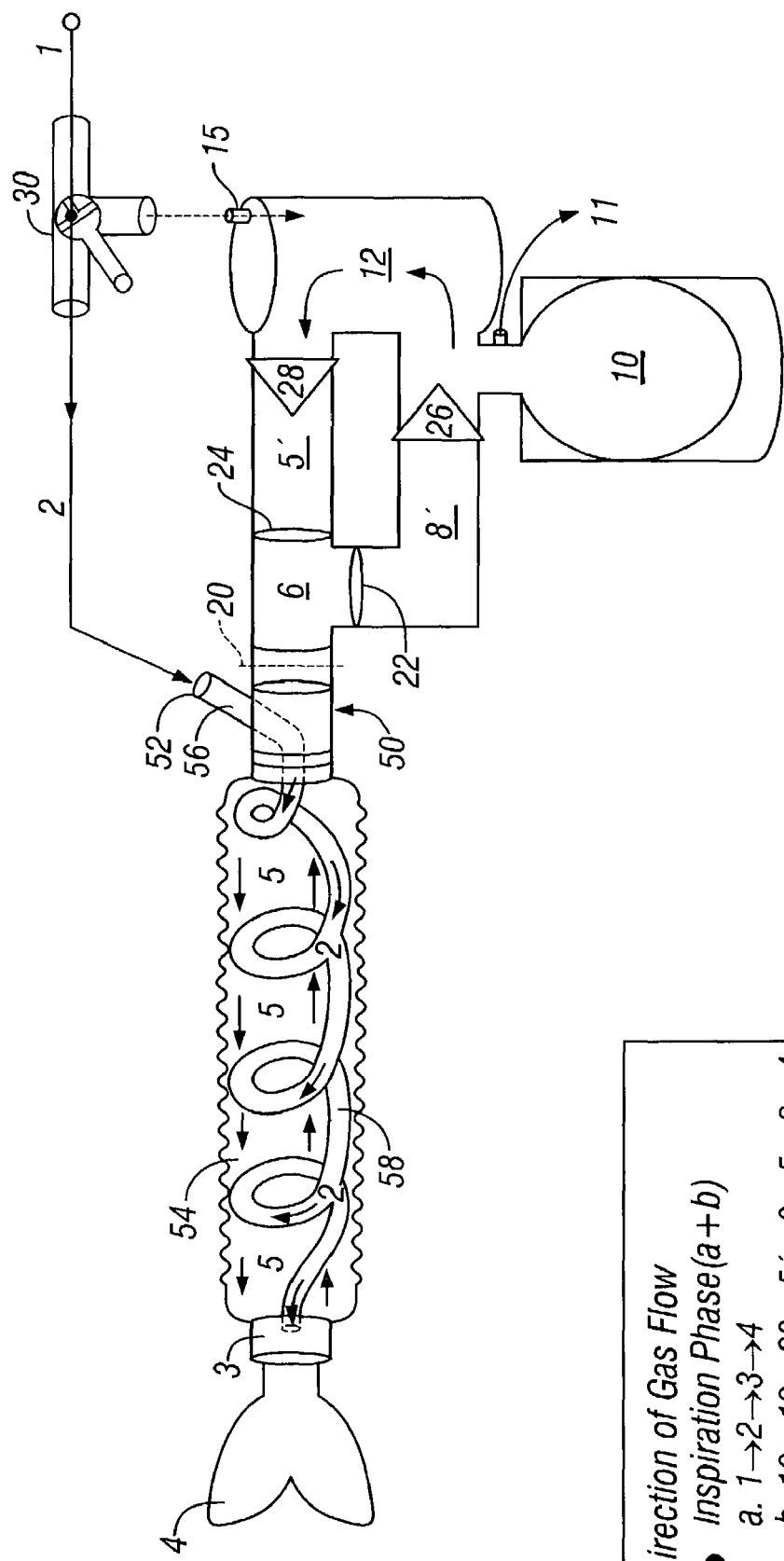
FIGS. 2A & B illustrate the components and operation of a F-COMBO™ system constructed in accordance with the present invention.
Figure 2B:
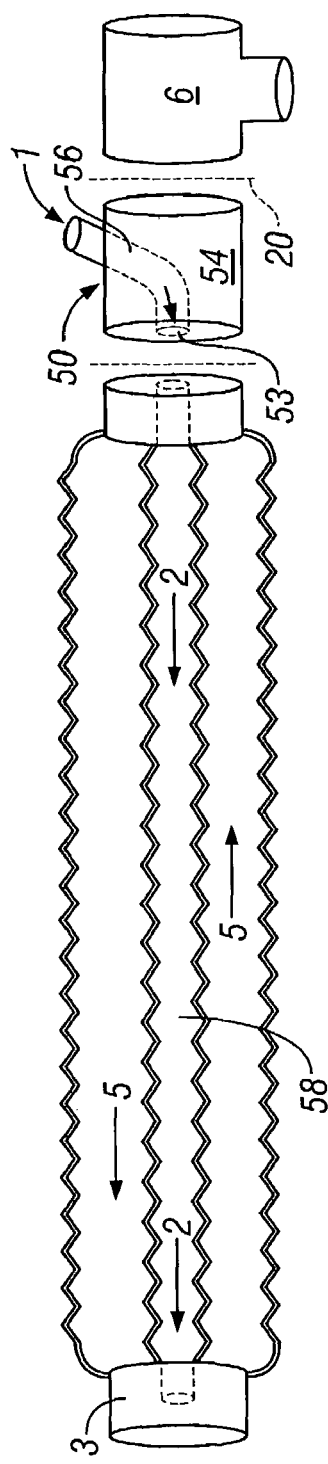
Figure 2C:
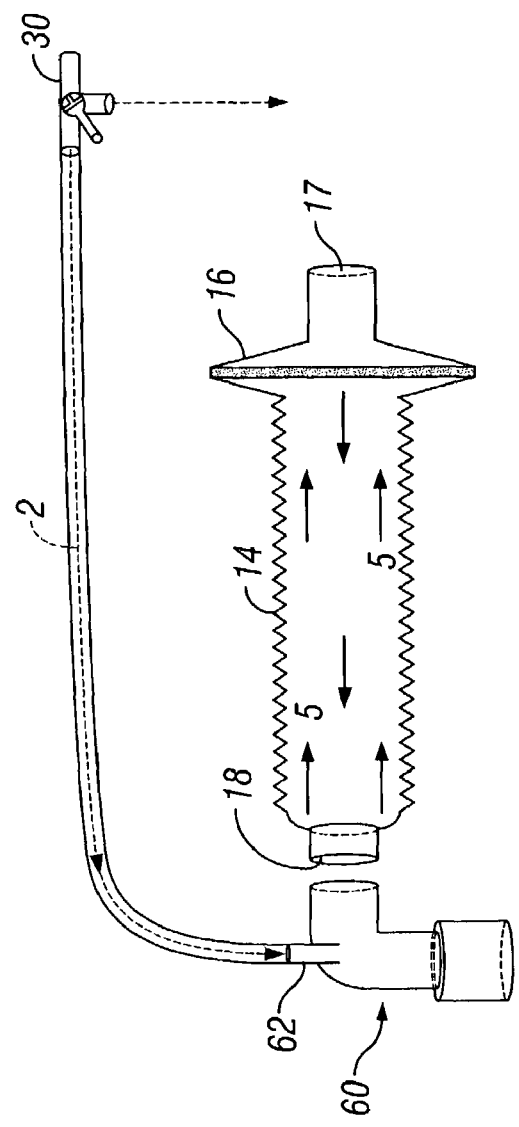
FIG. 2C illustrates a portion of an alternative embodiment of a circuit for an F-COMBO™ system operatively connected to an F-diverter™.

With reference to FIG. 2C, an alternative COMBO circuit is illustrated in partial schematic and cross-sectional form. A single lumen conduit 14 serves as the common breathing tube. A filter housing 16, containing a filter, may be integrally attached as shown, or connected in a standard manner to the proximal end of conduit 14. The proximal end of conduit 14 is connectable to flow splitting component 6 in FIGS. 2A and 2B, while FGF tube 2 is likewise connected to diverter 30. The distal end 18 of conduit 14 is connectable to patient fitting 60, which includes an FGF conduit 62. The length of rebreathing conduit 14 can be adjusted to adjust the internal volume. Conduit 14 may be formed of ULTRA-FLEX® tubing, or other suitable adjustable length tubing. Components, such as fitting 60, valve 30, and/or conduit 14 may be individually or provided in kit form.

Thus, in an embodiment, a new ventilation and anesthesia system is provided, comprising a recirculation module, a rebreathing tube operatively connected at its proximal end opening to the recirculation module for providing expired gases to and receiving gases from the recirculation module, and a distal input for fresh gases. The distal input is located in the distal portion of the rebreathing tube, or in a distal fitting operatively connected to the distal end of the rebreathing tube. The fresh gas flow input may be located at the proximal end of the rebreathing conduit, as illustrated in FIGS. 2A and B, and directed through the rebreathing conduit to the distal end thereof via an appropriate tube, or the FGF input may be at the distal end of the circuit.

The recirculation module preferably includes a scrubbing circuit, which may include at least two unidirectional valves, an expiratory input conduit, $CO_2$ absorber, exhaust vent, scrubbed gas output conduit, squeeze bag and/or ventilator.

F-conomy™ Systems

In the prior art circle system, fresh gases are directed into the scrubber module proximally of the inspiratory valve (i.e., "pre-inspiratory valve fresh gas flow input"). Post-inspiratory valve connection to a fresh gas flow line was believed to lead to excessive loss of fresh gases. Therefore, it was surprising to discover that low flow post-inspiratory valve FGF led to inspired concentrations of anesthetic gases more closely related to the delivered concentrations. This invention has significant gas saving and other benefits (e.g., reducing the hazards of breathing gases affected by the interaction of fresh gases with the soda lime in the scrubber). In the present invention, fresh gases are introduced continuously, including during the expiratory phase, into the inspiratory conduit, which acts as a reservoir for the fresh gases. Fresh gases in the reservoir and scrubbed gases flowing from the recirculation module are inspired during the inspiratory phase, and a portion of the expired gases are recirculated, scrubbed and reused as schematically shown in FIGS. 3-6.

With reference to FIGS. 3A-C and FIGS. 9A & F, the components and operation of an F-conomy™ system constructed in accordance with present invention are illustrated. Similar or identical parts used in the devices shown in FIGS. 1 and/or 2 are likewise numbered in FIGS. 3A-C. Gas flow arrows are numbered in this Figure as in the prior figures to facilitate understanding. An anesthesia machine has a fresh gas supply source 100, which includes flow meters 102 and 104 for providing gases such as oxygen and nitrous oxide, with appropriate readouts and controls familiar to one of ordinary skill in the art. A vaporizer 106 is connected in line with the output from the flow meters, so that volatile anesthetic agents can be carried to fresh gas output 108.

A diverter valve 110 with control lever 112 is placed in line with the fresh gas supply line 114. The diverter valve includes two intersecting conduits 116 in a cylindrical rotatable stopper, mounted in a matching seat of a valve housing at the junction of the diverter valve input conduit 118 and output conduits 120 and 122. Lever 112 can rotate the stopper in the housing. When lever 112 is aligned with output conduit 122, fresh gas cannot flow to output conduit 122, and fresh gas can flow to output conduit 120. When lever 112 is aligned with output conduit 120, fresh gas can flow to output conduit 122 but not to output conduit 120. When the lever 112 is in between the output conduits, depending on the width of the conduits in the valve, fresh gases may simultaneously flow to both output conduits. When lever 112 is aligned with input conduit 118, flow through the diverter valve is blocked; in the event this is not be desired, a lever-stop can be installed to prevent the valve from being rotated into a completely closed position.

In an alternative embodiment, the FGF diverter of the present invention may comprise a manifold which receives FGF in an input conduit and directs it to a plurality of output conduits. Each of the output conduits can have a separate flow control. For example, two output conduits could be fully or partially opened to permit varying levels of fresh gas to simultaneously flow to scrubber FGF input and to a post-inspiratory valve FGF input. The flow controls can be manually operated or electromechanically operated with appropriate integration with the assisted ventilation system processor and controls.

Figure 3A:
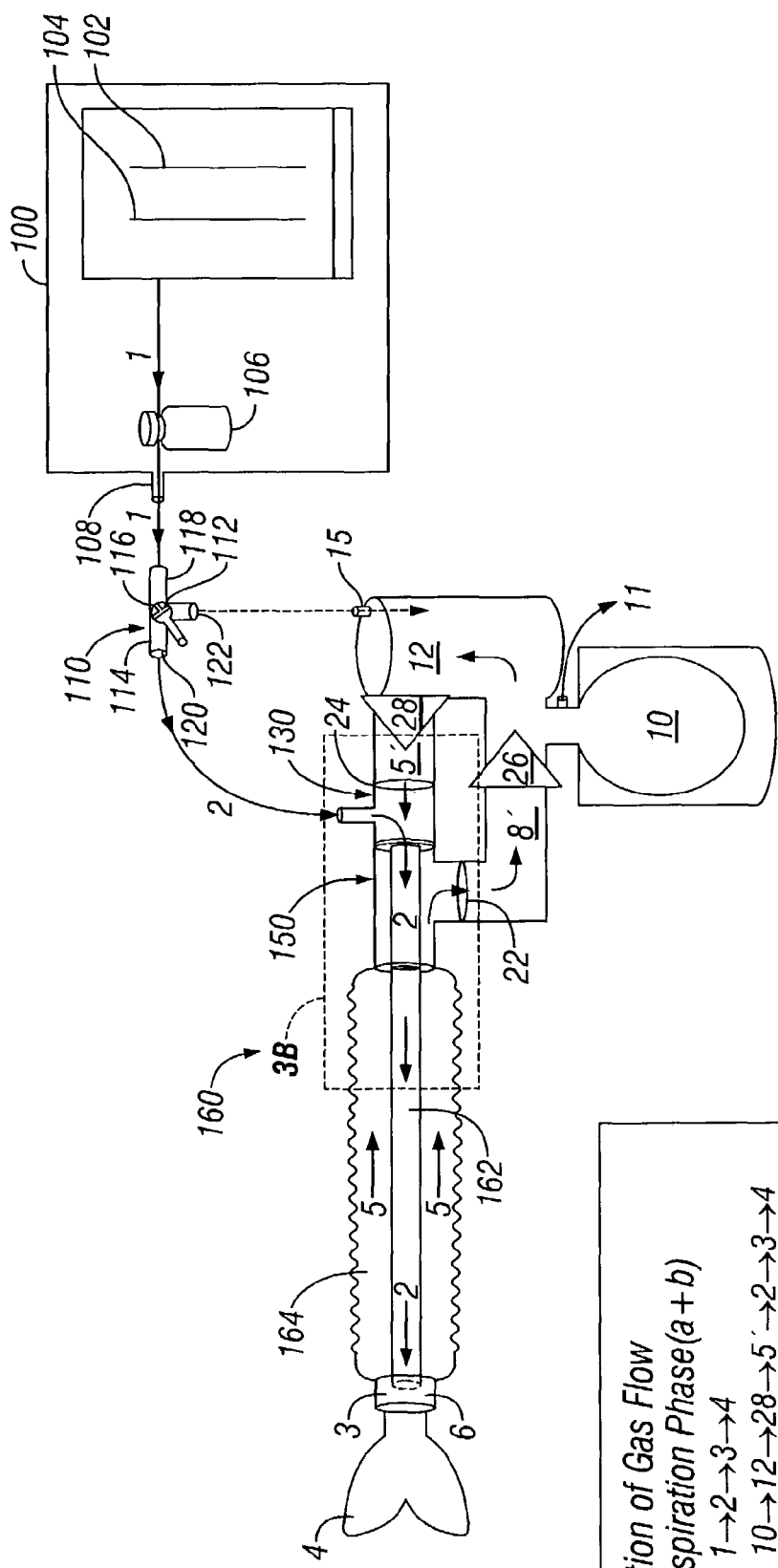
FIGS. 3A-C illustrate the components and operation of an F-conomy™ system constructed in accordance with present invention.
Figure 3B:
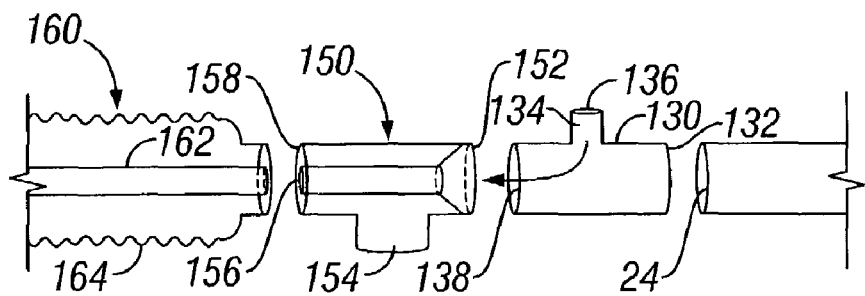

When fresh gas is permitted to flow out of conduit 122, it will flow into a fresh gas input port 15 on scrubber 12, whereas when fresh gas is permitted to flow out of conduit 120, it can be directed to a fresh gas flow adapter 130 in breathing circuit 160. An exploded partial schematic view of the proximal end of breathing circuit 160 is illustrated in FIG. 3B. Scrubbed gases coming from inspiratory port 24 are led into the proximal port 132 of adaptor 130 and flow out of distal port 138. Fresh gases from fresh gas source 100 are directed to the inspiratory path conduit of adaptor 130 via fresh gas input 136 into fresh gas flow conduit 134. Exemplary proximal adaptors 130 are separately illustrated in FIGS. 9A and 9F.

Component 150 may be recognized as a Universal F2® proximal terminal having a coaxial arrangement of the inspiratory and expiratory conduits. The F2™ inventions described in U.S. Pat. No. 5,778,872 pioneered the use of multilumen proximal terminals and multilumen fittings that could be readily connected to form breathing circuits, whether the tubes in the fittings are coaxial, in apposed or parallel closely spaced relationship, or share a common wall. The proximal fitting can be readily disconnected from the proximal terminal at the site of use by a user.

In the exemplary system illustrated, the proximal terminal includes an inspiratory port 152 for operative connection to distal port 138 of the adapter 130, and an expiratory port 154 for operative connection to the expiratory port 22 in the recirculation module. Inspiratory port 152 is shown with a conical interior tapering to facilitate understanding that the gases flowing from adaptor 130 would only flow to the inner tube to port 156; however, port 152 would be appropriately shaped and dimensioned to mate with port 138 of adaptor 130.

Distal or patient ports 156 and 158 are connectable to a flexible unilimb respiratory conduit 160, having an inner conduit 162 and an outer conduit 164. In a preferred embodiment, the conduits 162 and 164 are connected at their proximal end to a proximal fitting, not shown for purposes of facilitating description of the invention, which in turn may be readily connected and disconnected from the proximal terminal by a user at a site of use. Note that inspiratory tube 162 is in fluid communication with inspiratory port 24 through adaptor 130 and the inspiratory conduit of proximal terminal 150 (i.e., fresh and scrubbed gases flow into inspiratory conduit 162). This is in contrast to the system of FIGS. 2A & B, in which gases coming from the scrubber at port 24 may only flow to outer tube 5, which functions both as the inspiratory tube during inspiration and as the expiratory tube during expiration (this is indicated by the flow arrows in opposite directions). FIGS. 3A & B operates as a circle system so flow in inspiratory tube 162 is towards the patient, while flow in the outer flow path 5 (e.g., in expiratory tube 164 proximal to the distal end of tube 162) is away from the patient.

Figure 3C:
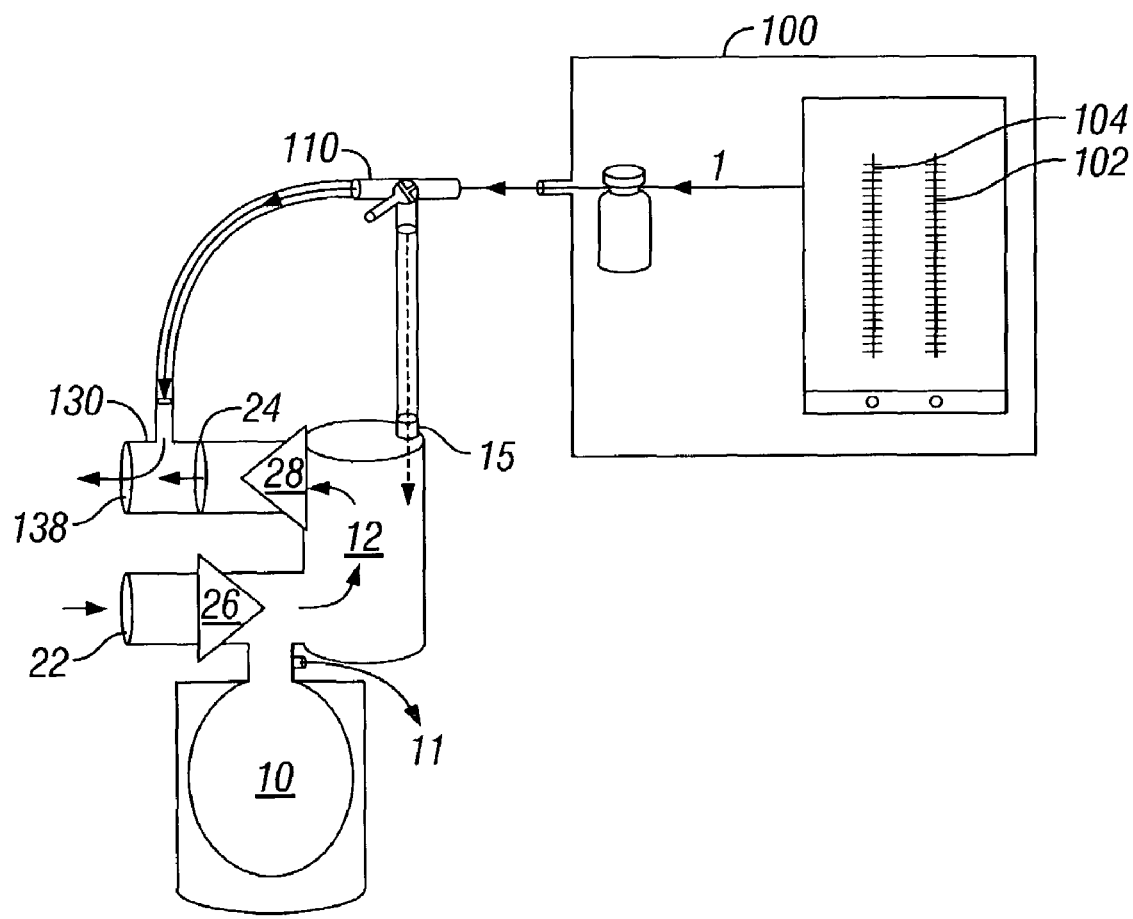

FIG. 3C illustrates a preferred embodiment of the F-scrubber operatively attached to a gas source 100. In one embodiment, adaptor 130 and diverter 110 can be provided as a kit to modify a scrubber module as schematically shown. In another exemplary embodiment, the F-scrubber comprises the scrubber module and the diverter valve 110 (connectable to but without adaptor 130 or gas source 100). In another exemplary embodiment, the F-scrubber comprises the scrubber module and the adaptor 130 (connectable to but without the diverter valve 110 or gas source 100).

The system of FIGS. 3A & B can be readily formed by modifying an existing assisted ventilation system to use the diverter valve, and by connecting adapter 130 at the proximal end of any circuit, for example a circuit with a F2™ proximal terminal at its proximal end. Hence, the significant and surprising improvements in assisted ventilation systems and components brought about by the F2™ inventions can now be further enhanced with post-inspiratory valve fresh gas flow input. This is facilitated in an embodiment by addition of the new proximal adapter of the present invention, a non-limiting example of which is illustrated in FIG. 3B.

Figure 5:
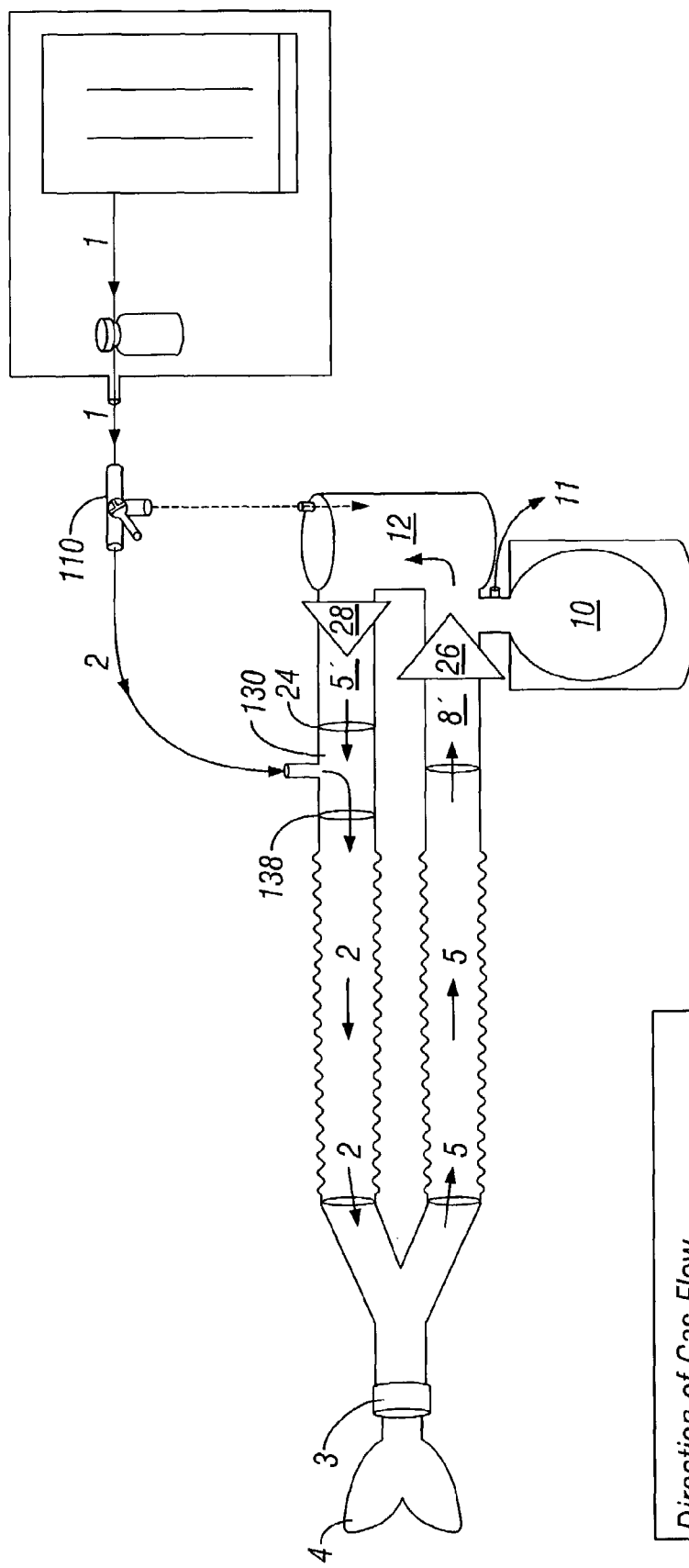
FIG. 5 illustrates a dual limb, rather than unilimb, F-conomy™ system constructed in accordance with the present invention.
Figure 9A:
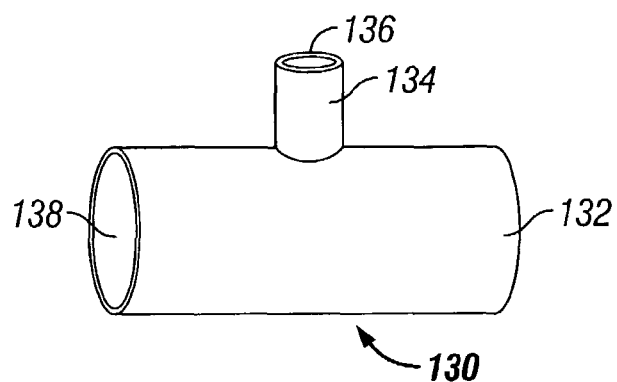
FIGS. 9A-F illustrate fresh gas flow adapters constructed in accordance with the present invention, as well as multilumen proximal fittings and proximal terminals incorporating a fresh gas flow input.
Figure 9B:
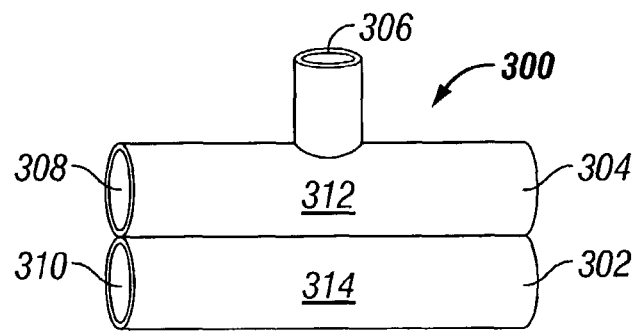
Figure 9C:
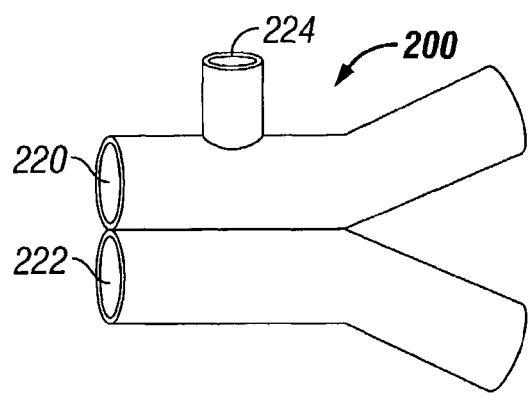
Figure 9D:
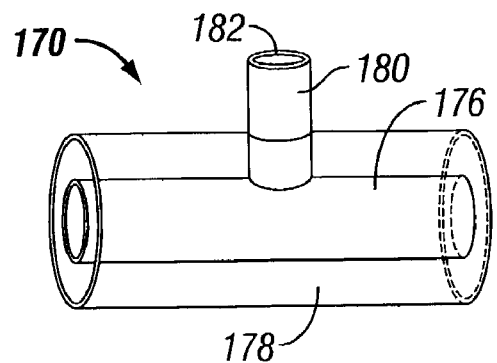
Figure 9E:
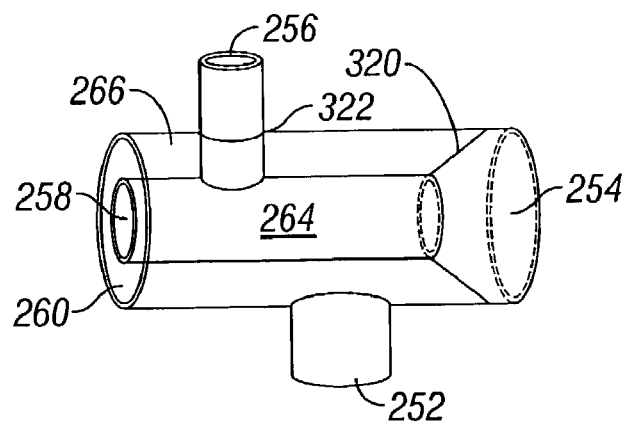
Figure 9F:
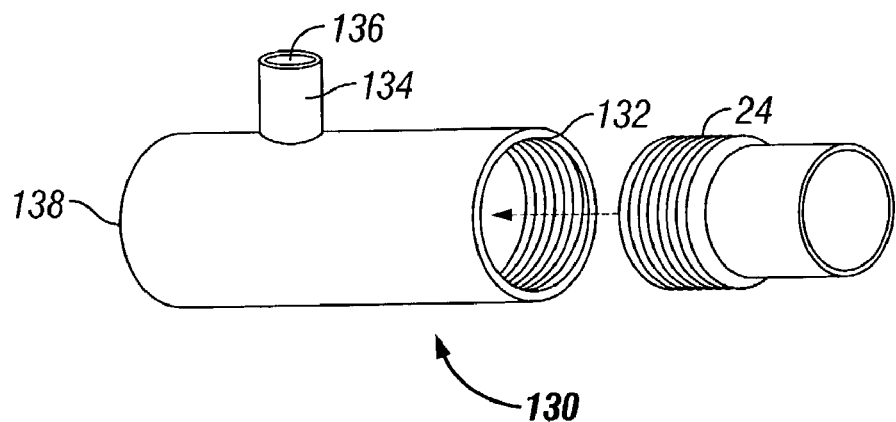

With reference to FIG. 9F, inspiratory port 24 may be provided with threads corresponding to those in the proximal end 132 of adaptor 130, for example as in the system configuration of FIG. 5, to provide for permanent or semi-permanent attachment together. A variety of connecting and blocking means may be utilized on components of the present inventions to only permit connection to matching components. For example, threads may also be placed at the distal port 138 for connection to components with mating threads.

Figure 4:
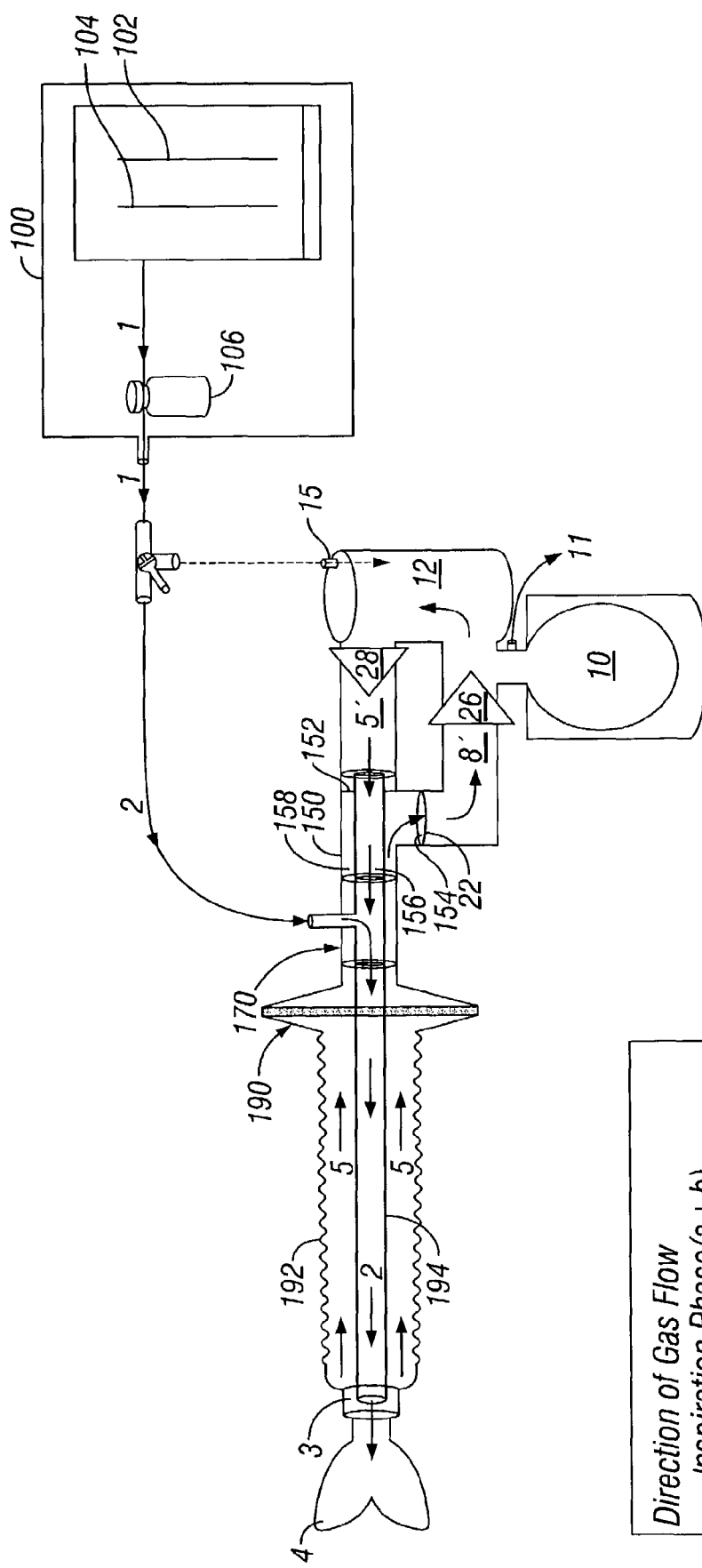
FIG. 4 illustrates another embodiment of an F-conomy™ system constructed in accordance with present invention.

With reference to FIG. 4, another embodiment of an F-conomy™ system constructed in accordance with the present invention is illustrated. In this embodiment, the fresh gas flow input is placed distally of an F2 proximal terminal 150. Gas flow arrows are numbered in this Figure as in the prior figures to facilitate understanding. A novel multilumen proximal fitting 170, individually illustrated in FIG. 9D is operatively connected to the patient ports 156 and 158 of the proximal terminal 150. An inner lumen 176 is connected to port 156 while an outer lumen 178 is connected to port 158. Fitting 170 and Terminal 150 are formed of rigid materials as disclosed in U.S. Pat. No. 5,778,872, which materials are generally thicker or more rigid than the materials forming the flexible tubing carrying gases to and from the patient. Lumens 176 and 178 are formed of concentric pipes that are kept in spaced relationship by a rigid integral FGF conduit 180. FGF conduit 180 has an FGF input 182 and connects at its opposite end to inner conduit 176. While FGF conduit 180 will only generally have a diameter suitable for FGF input, inner conduit 176 preferably has a sufficient cross-sectional area to serve as part of an inspiratory conduit. However, if the flow patterns in the system were reversed, in an embodiment, the FGF conduit 180 could connect to outer conduit 178 (which would have a suitable cross-sectional area to act as an inspiratory conduit). Multilumen proximal fittings of the present invention (F3 proximal fittings) enable ready connection of fresh gas flow distally of an inspiratory valve in a system using a F2 multilumen proximal terminal.

A multilumen filter 190 is shown connected to the distal end of fitting 170. The inner and outer lumens of the filter housing may be integral with flexible respiratory conduits 192 and 194, or detachable. While FIG. 10C combines the features of filter 190 with a fresh gas flow input, the operation and construction are otherwise substantially similar.

FIG. 5 illustrates a dual limb, rather than unilimb, F-conomy™ system constructed in accordance with the present invention. A standard dual limb circle system is modified to incorporate diverter valve 110 and proximal adapter 130. The system permits ready switching of fresh gas flow input from the scrubber 12 to a post-inspiratory valve input and vice versa.

Figure 6:
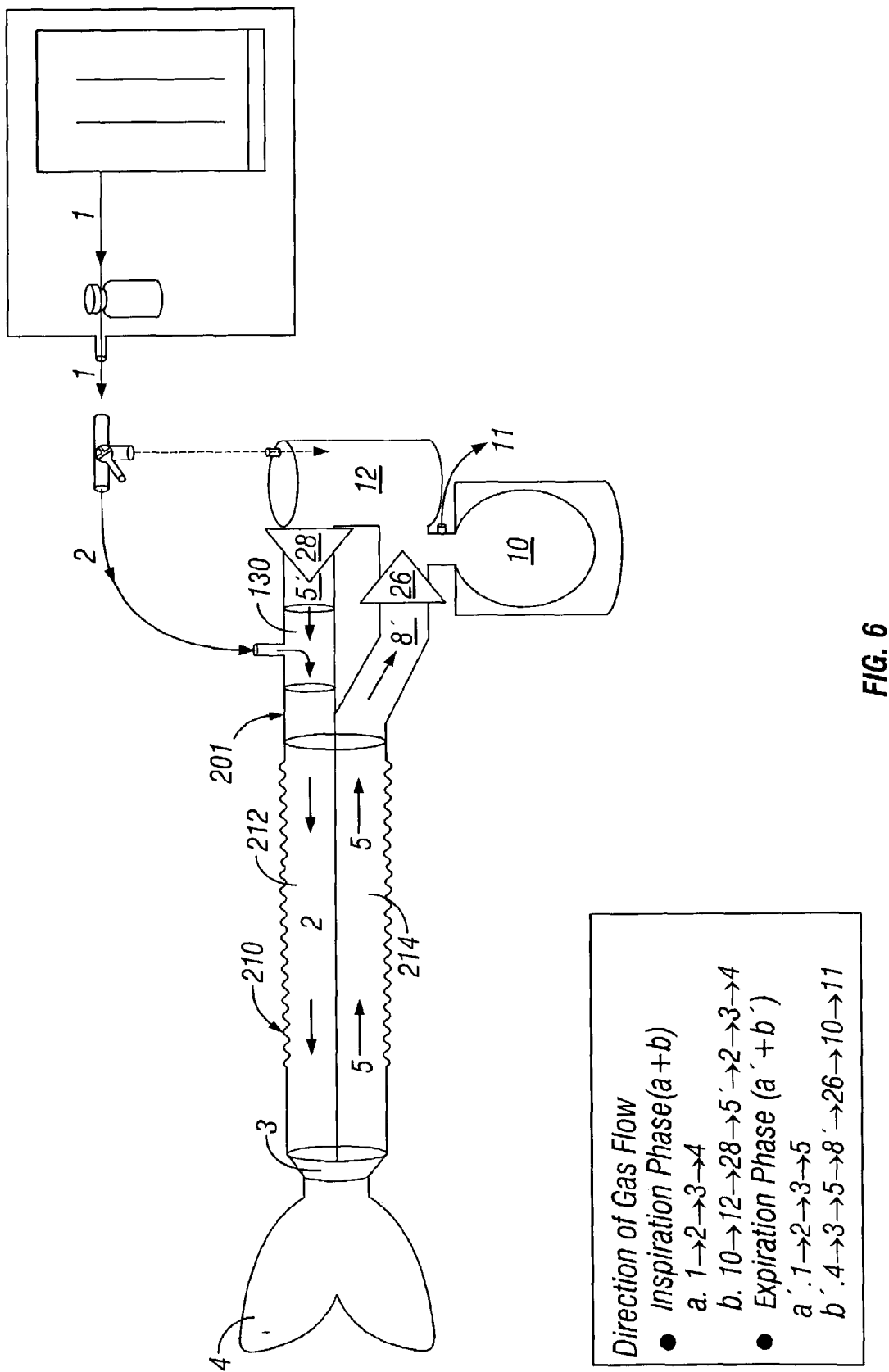
FIG. 6 illustrates an alternative F-conomy™ system of the present invention.

The system of FIG. 6 operates in substantially the same fashion as that of FIG. 5. The systems differ only in that a multilumen proximal terminal 201 merges the independent flows into a unilimb multilumen conduit 210. Terminal 201 is substantially the same as terminal 200 shown in FIG. 9C, except that terminal 201 in FIG. 6 does not include the FGF conduit 224 of the terminal in FIG. 9C, The conduit 210 has an inspiratory lumen 212 and an expiratory lumen 214. The lumens 212 and 214 can be adhered directly to the distal ends of the proximal terminal 201, e.g., ports 220 and 222 in FIG. 9C, or connected thereto by an F2 proximal fitting which provides for simultaneously connecting plural parallel conduits to a multilumen terminal.

Figure 7:
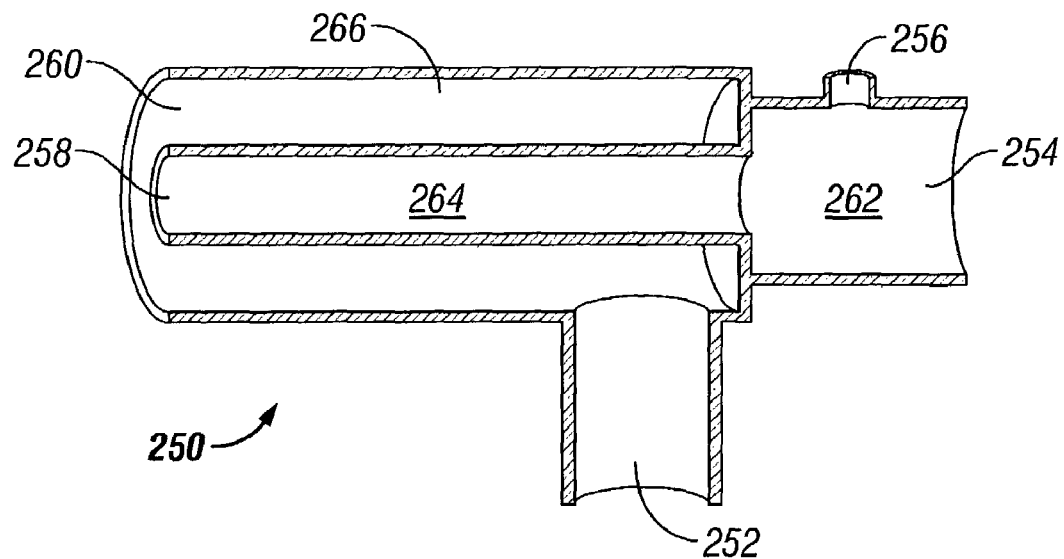
FIG. 7 illustrates in cross-sectional view an F3™ proximal terminal of the present invention.

FIG. 7 illustrates in cross sectional view an exemplary embodiment of an F3™ proximal terminal 250 of the present invention. The terminal is substantially the same in construction as a coaxial Universal F2® proximal terminal, except it can also serve as a post-inspiratory valve fresh gas flow adapter by provision of a fresh gas flow input. The terminal is preferably made of metal for permanent or semi-permanent attachment to an assisted ventilation machine or of rigid medical grade plastic where routine disposal is likely.

Terminal 250 includes a machine expiratory port 252, a scrubbed gas inspiratory port 254, a fresh gas flow input port ("FGF port") 256, a patient inspiratory gas port 258, and a patient expiratory gas port 260. Like an F2 proximal terminal, the inspiratory port 254 is operatively connectable to the machine inspiratory port distal of the inspiratory valve, and the expiratory port 252 is operatively connectable to the machine expiratory port. A coaxial F2 proximal fitting and circuit components can be connected to ports 258 and 260. Fresh gas provided at the FGF port 256 flows into proximal inspiratory lumen 262, to distal inspiratory lumen 264 and out of port 258. Expiratory gases flow into expiratory lumen 266 from port 260 and out of expiratory port 252. While a coaxial embodiment is illustrated here, the embodiments shown in FIGS. 9C and 9E (discussed below) illustrate that an F3 proximal terminal can have a variety of configurations.

Figure 10A:
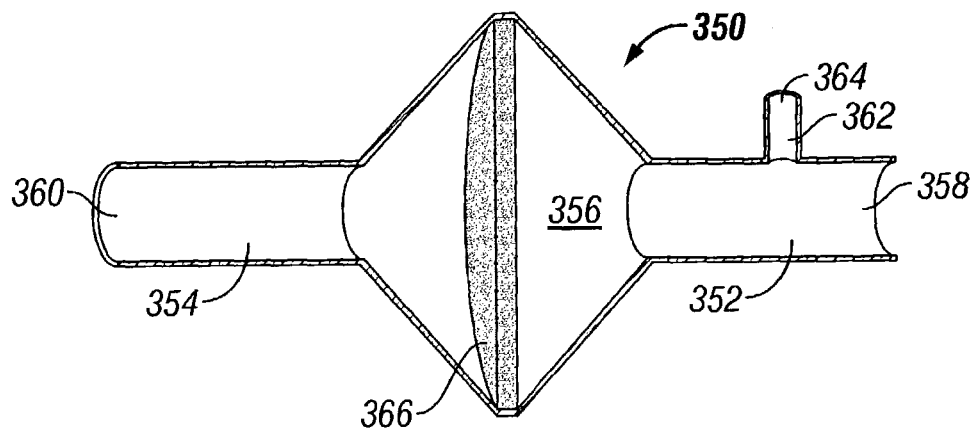
FIG. 10A illustrates in cross-sectional view a monolumen filter of the present invention incorporating a fresh gas flow input.
Figure 10B:
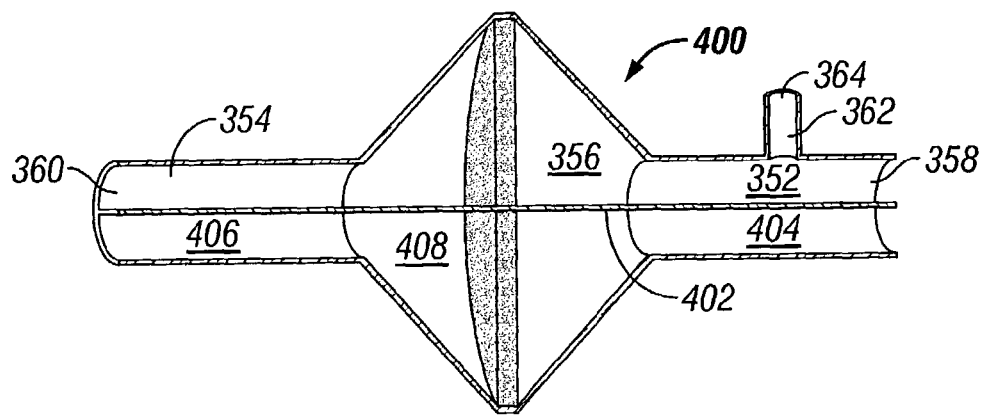
FIG. 10B illustrates in cross-sectional view a multilumen filter of the present invention in which one lumen incorporates a fresh gas flow input.
Figure 10C:
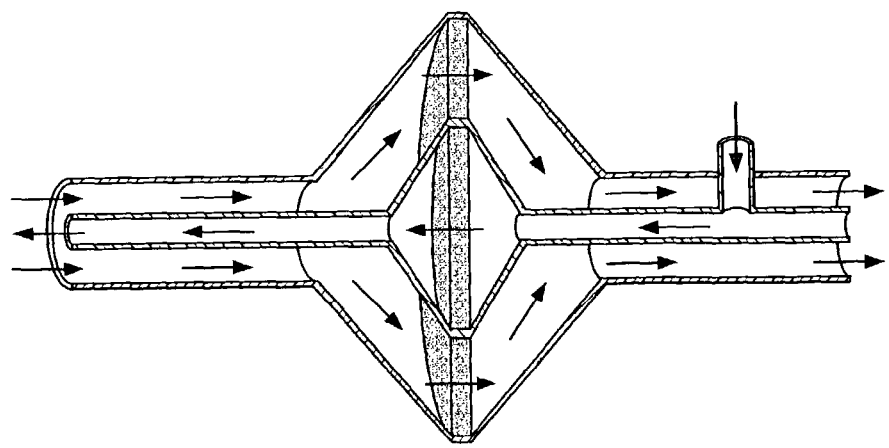
FIG. 10C illustrates in cross-sectional view a co-axial form of the multilumen filter of FIG. 10B incorporating a fresh gas flow input in one lumen; flow paths therein are shown with arrows (part numbers are not included to facilitate understanding of the flow paths). These filters can serve as proximal fittings and fresh gas adaptors.

In an embodiment, lumen 264 and/or lumen 266 may include an inline filter chamber with a filter therein. Filter means can be formed substantially as shown in FIG. 10B or 10C.

Figure 8:
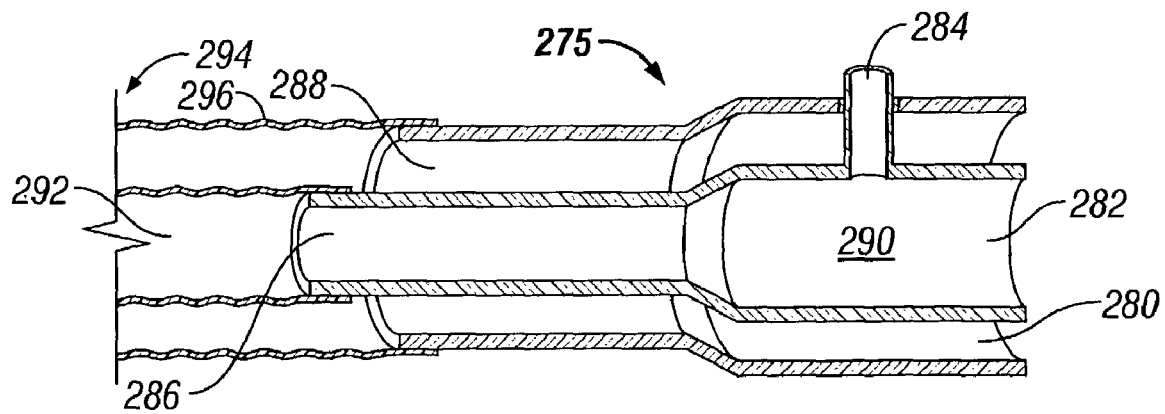
FIG. 8 illustrates in cross-sectional view an F3™ proximal fitting of the present invention.

FIG. 8 illustrates in cross-sectional view an F3™ proximal fitting of the present invention. The fitting is substantially the same in construction as a coaxial Universal F2® proximal fitting, except it can also serve as a post-inspiratory valve fresh gas flow adapter by provision of a fresh gas flow input. Fitting 275 includes a machine expiratory port 280, a scrubbed gas inspiratory port 282, a fresh gas flow input port ("FGF port") 284, a patient inspiratory gas port 286, and a patient expiratory gas port 288. Like an F2 proximal fitting, the inspiratory port 282 is operatively connectable via a corresponding Universal F2 proximal terminal to the machine inspiratory port distal of the inspiratory valve, and the expiratory port 280 is likewise operatively connectable to the machine expiratory port.

FGF flow from FGF input port 284 mixes with scrubbed gas flow in inner lumen 290, which is operatively connected in the illustrated embodiment to the inner flexible conduit 292 of a multilumen patient respiratory conduit 294. The inner conduit is contained within an outer flexible conduit 296, which maintains the coaxial flow of the inspiratory gases in the inner conduit and expiratory gases in the outer conduit from the fitting 275. In an embodiment, the fitting 275 is provided with conduits 292 and 296 permanently bonded thereto. In another embodiment, the conduits can be connected to a multilumen filter and then to the fitting. While a coaxial embodiment is illustrated here, the embodiments shown in FIGS. 9B and 9D (discussed further below) illustrate that a F3 proximal fitting can have a variety of configurations.

FIG. 9B illustrates an alternative F3 proximal fitting 300. Fitting 300 includes a machine expiratory port 302, a scrubbed gas inspiratory port 304, a fresh gas flow input port ("FGF port") 306, a patient inspiratory gas port 308, and a patient expiratory gas port 310. Like an F2 proximal fitting, the inspiratory port 304 is operatively connectable via a corresponding Universal F2 proximal terminal to the machine inspiratory port distal of the inspiratory valve, and the expiratory port 302 is likewise operatively connectable to the machine expiratory port.

The first tube 312 forming the inspiratory lumen is in parallel apposed spaced relationship to the second tube 314 forming the expiratory lumen. By making appropriate dimensional adjustments (and provision of a gap between the opposite ends of the tubes 312 and 314 where needed for the fittings to form a fluid tight junction) ports 302 and 304 can be operatively connected to a corresponding F2 proximal terminal. For example, the F3 proximal terminal of FIG. 9C would form an F2 proximal terminal if it did not have FGF port 224, in which case, ports 302 and 304 could connect to ports 220 and 222 respectively.

FIG. 9E illustrates an alternative embodiment of the F3 proximal terminal of FIG. 7. The terminals are substantially identical with like parts numbered accordingly, except that the inspiratory port 256 has been moved so as to merge with the distal inspiratory lumen 264. In this embodiment the combination of the annular wall 320 and the junction 322 of the walls of the fresh gas conduit and the outer lumen 266 reinforce the spaced relationship of the inner and outer lumens. Annular wall 320 is shown with a conical interior tapering to facilitate understanding that the gases flowing from a fitting connected thereto would only flow to the inner tube 264 and to port 258; however, in practice, port 254 would be appropriately shaped and dimensioned to mate with a corresponding fitting.

As should be clear from the foregoing, a wide variety of components can be formed for providing post-inspiratory valve FGF input. These components can be further modified to include filters. In the alternative, unitary circuits or substantial portions thereof, can be formed to incorporate many different features in combination with a post-inspiratory valve FGF input. For example, FIG. 10A illustrates in cross-section a monolumen filter of the present invention, which incorporates a fresh gas flow input. Hence, filter 350 can be used as a proximal (or distal) FGF adaptor in accordance with the present invention.

A housing 350 includes a proximal lumen 352, a distal lumen 354, and a filter compartment 356 all in fluid communication with proximal and distal ports 358 and 360. A FGF input conduit 362 has an FGF input 364 and preferably connects to lumen 352. A filter 366 of appropriate quality and surface area to achieve desired filtration and flow rates is provided as one of ordinary skill in the art would understand (e.g., filter dimensions and properties can match those provided by King Systems Corporation of Noblesville Ind., USA for monolumen filtration). It is preferred that the fresh gases be filtered prior to provision to the patient, but it is envisioned that the FGF input conduit could be distal of the filter.

FIG. 10B illustrates a multilumen filter 400 of the present invention in which one lumen incorporates a fresh gas flow input. Lumens 352 and 354 and filter compartment 356 function the same in FIGS. 10A and B, so that the filter of 10B functions essentially the same way as that of FIG. 10A. However, the multilumen filter of FIG. 10B provides for simultaneous filtration of two independent lumens, while eliminating the need for providing, tracking, connecting and disconnecting two separate filters. The filter 400 can act as a proximal fitting in the same manner as the embodiments shown in FIG. 9B. All of the components of FIG. 10A are present, but the shapes have been adjusted so that a common wall 402 is shared by both flow paths and filter housings. A second or expiratory flow path is formed by a proximal lumen 404, a distal lumen 406, and a second filter chamber 408.

FIG. 10C illustrates a co-axial version of the multilumen filter of FIG. 10B. A fresh gas flow input is provided in one lumen. Flow arrows demonstrate a preferred direction of flow.

Figure 11:
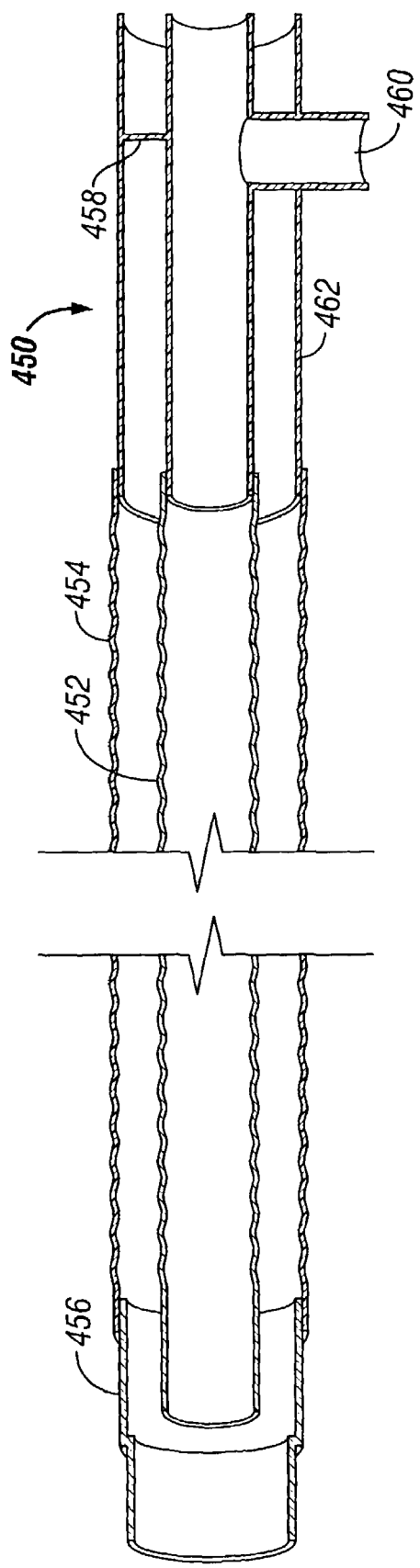
FIG. 11 illustrates in partial cross-sectional view a unitary co-axial multilumen respiratory circuit incorporating a fresh gas flow input in a multilumen proximal fitting that can be utilized with a Universal F2® coaxial proximal terminal.

FIG. 11 illustrates in partial cutaway view a unitary co-axial multilumen respiratory circuit incorporating a fresh gas flow input on a proximal fitting that can be utilized with a Universal F2® coaxial proximal terminal. In other words, an F3 proximal fitting 450, such as that illustrated in FIG. 9D or 9B is permanently bonded to appropriate flexible conduits 452 and 454, which in turn may terminate in a distal fitting 456. This circuit may include a filter, in the same fashion as illustrated in FIG. 10B or 10C depending on the relationship of the lumens forming the circuit. FGF conduit 460 is integral with the wall of the outer pipe 462, and will maintain the fixed spaced relationship of the inner and outer pipe. Fitting 450 may include one or more flanges or struts, such as strut 458, to help maintain the spaced relationship of the rigid pipes or tubes forming the fitting. This may be desired if it is believed that torsional stresses on the fresh gas flow input conduit coupled with stress on the two pipes from the tubes 452 and 454 might contribute to weakening of the device.

Figure 12:
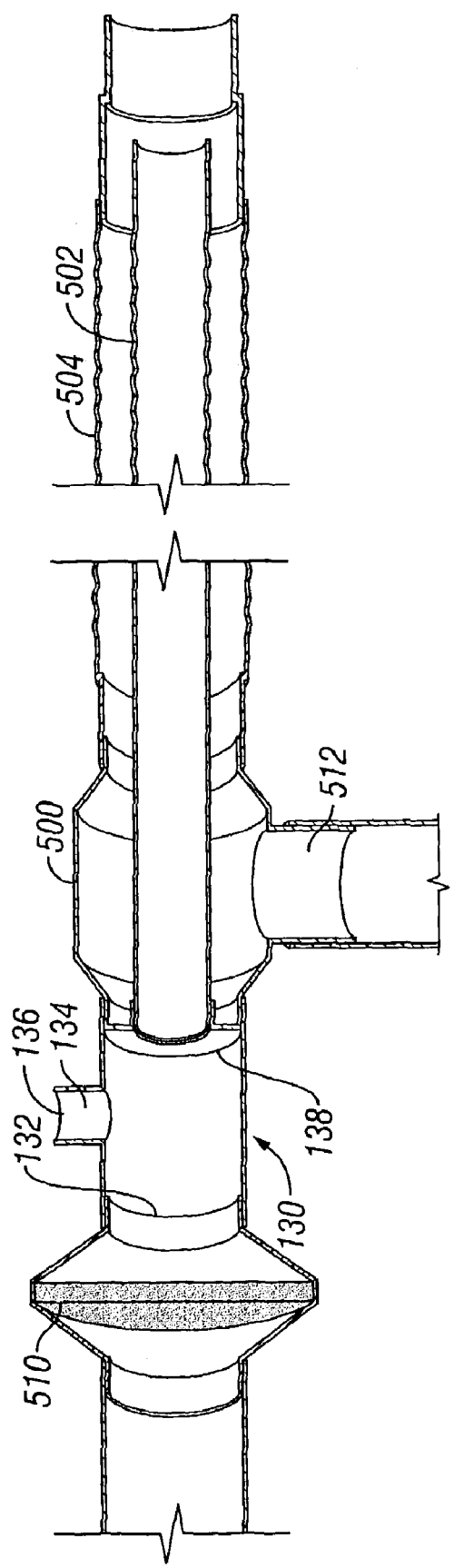
FIG. 12 illustrates in partial cross-sectional view a Universal F® type unitary circuit modified with an FGF adapter to have a fresh gas flow input proximally of the proximal terminal.

FIG. 12 illustrates a modified Universal F® unitary respiratory circuit in partial cross-sectional view to which an FGF adapter 130 has been added proximally of the proximal terminal 500. The Universal F® circuit is a predecessor of the Universal F2®, so its proximal terminal 500 is rigidly bonded to the respiratory conduit inner and outer flexible conduits 502 and 504. The proximal terminal does not provide for ready attachment or detachment to flexible respiratory conduits. In the illustrated embodiment, a filter 510 is connected to the proximal port 132 of the adaptor 130 and to the inspiratory port of an assisted ventilation machine. Adaptor 130 is connected at port 138 to the inspiratory port on the proximal terminal. Expiratory port 512 is connectable to an expiratory port on the assisted ventilation machine. The circuit may be used in performing methods of the present invention by having fresh gas flow from the machine diverted to the FGF input 136 distally of the inspiratory valve.

EXAMPLES

The following hypotheses were tested: a) The inspired and the delivered fresh gas concentration (FI/FD) ratio is dependent on the fresh gas flow (FGF) over time; and b) Using a gas saving system of the present invention (e.g., F3™ COMBO system) the $F_I/F_D$ ratio can be improved at low flows.

The effects of lower FGF on patients' inspired gas concentrations were compared to the delivered gas concentrations (i.e., anesthetic concentrations indicated by the vaporizer's dial setting) during general anesthesia.

After obtaining institutional approval and patient consent, a total of 34 healthy (ASA class I) adult patients undergoing elective surgery were included in the studies. The studies were conducted using standard methods of anesthesia: Anesthesia was induced with thiopental and endotracheal intubation was facilitated with 1 mg/kg succinylcholine. Anesthesia was initially maintained with high flow (5 L/min) of 3/2 $N_2O$—$O_2$ mixture and 1.5% isoflurane as per vaporizer setting using the standard anesthesia circle system with $CO_2$ absorption. The patient's lungs were mechanically ventilated using the traditional mode of intermittent positive pressure ventilation with a tidal volume of 10 ml/kg, ventilation frequency (10-12 breaths/min) and inspiratory/expiratory ratio (1:2). The above parameters were kept constant throughout the study. Fraction of delivered ($F_D$), inspired (FI) and end-tidal (FET) anesthetic gas concentrations were continuously monitored by mass spectrometry (Medical Gas Analyzer 100; Perkin-Elmer, Pomona, Calif.).

Figure 13:
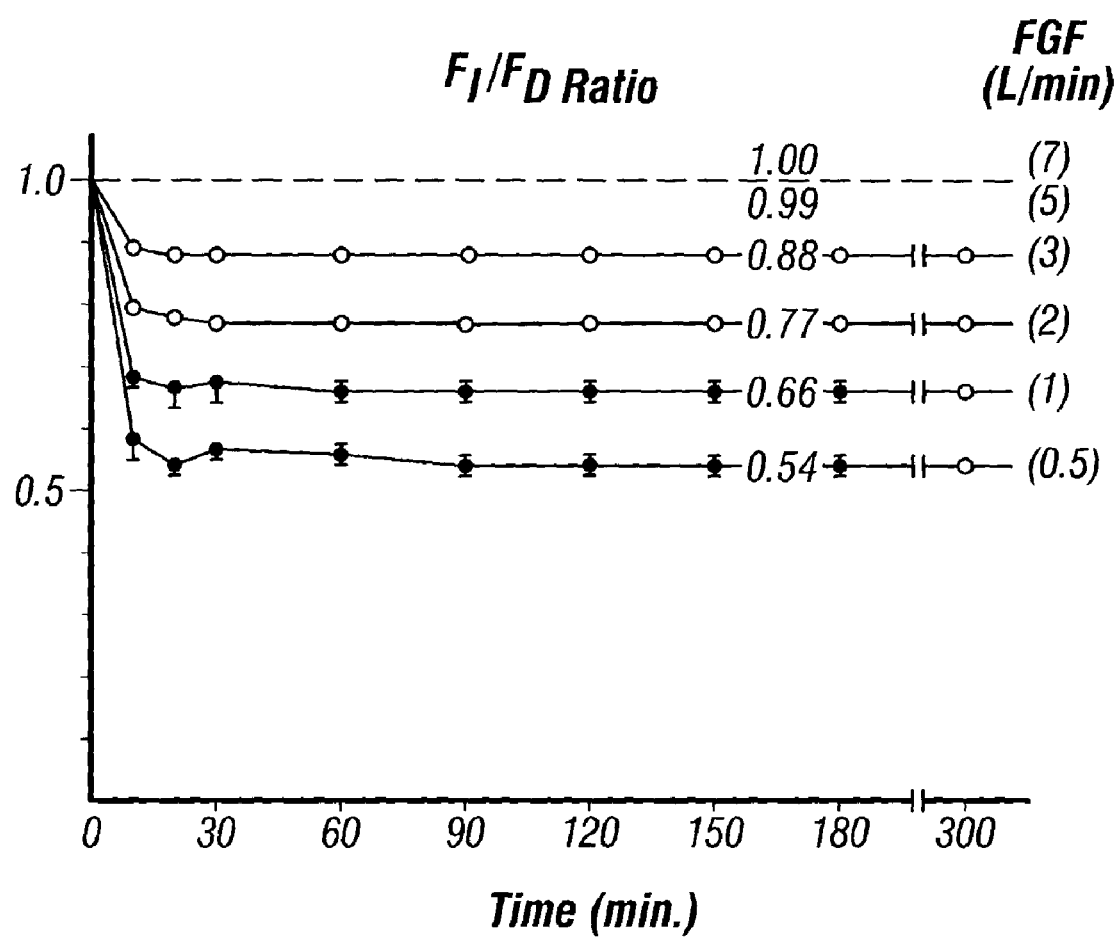
FIG. 13 is a graph illustrating the relationship of inspired ($F_I$) and delivered ($F_D$) isoflurane concentration during graded low fresh gas flow (FGF) anesthesia.

In study I, after 15 min of stabilization with high fresh gas flow (FGF>5 L/min), FGF was changed to lower FGF, selected from 4 L/min (n=3), 3 L/min (n=3), 2 L/min (n=3), 1 L/min (n=6) and 0.5 L/min (n=6), which was assigned randomly, while the same vaporizer setting (1.5% isoflurane) was maintained. Measurements of $F_I$ and $F_{ET}$ and $F_D$ were repeated for comparison of $F_I/F_D$ ratios and statistical analysis. The results of the study are summarized in FIG. 13. The results demonstrate that as the FGF is lowered the $F_I/F_D$ (or FI/FD) ratio is significantly decreased in a parallel way. Furthermore, the study shows that there is indeed a significant discrepancy between $F_I$ and $F_D$ and points out the limitations of low flow anesthesia when the conventional circle system is utilized.

Table 1 shows data from Study II, in which 12 patients were randomly assigned to group A using the conventional circle system (n=6) and to group B, using the F3™ COMBO system during a low flow anesthesia (1 L/min) FGF. Notice in Table 1 that the $F_I$ concentration and the $F_I/F_D$ concentration ratios are greatly improved in group B wherein the F3™ COMBO system is utilized. It also shows that the difference between the $F_I$ and $F_D$ are minimal and that the new system provides a better correlation. This supports the hypothesis that low flow anesthesia can be safely administered by using the F3 COMBO™ system, and over-dosing or under-dosing of anesthetics can be avoided. Substantially the same gas saving results can be achieved using the F-conomy system of the present invention.

With the present gas saving F3 COMBO™ and F-conomy™ systems, the anesthetist will be able to better control the inspired concentration of anesthetic gases in a more accurate and predictable manner. Therefore, even in the absence of expensive multi-gas monitoring equipment, a safe and reliable low flow anesthesia can be achieved. Also, recovery from anesthesia can be accelerated at the end of surgery and anesthesia. This can be accomplished by providing high flows of oxygen directly at the distal end so that the residual anesthetic in the lungs and the breathing circuit will be washed out very quickly. Quick recovery from anesthesia can save anesthesia recovery time and money. Therefore, the gas saving systems circuits of the present inventions, and/or methods for utilizing same, can conserve anesthetic gases as well as oxygen, while minimizing pollution and health hazards, and thus improve breathing/anesthesia system efficiency. This will result in overall lower health care costs while optimizing patient health care.

TABLE 1

Effect of diverting the FGF to the distal end of the circuit on the $F_I$ and $F_I/F_D$ ratio during low flow isoflurane anesthesia (1 L/min) using a conventional system versus the F3 COMBO ™ system

| Patient No. | Vaporizer Setting ($F_D$) Vol. % | Group A (n = 6) Without Diverting FGF* (i.e., FGF provided proximally of the inspiratory valve) | | Group B (n = 6) Diverting FGF** (i.e., FGF provided distally of the inspiratory valve) | |
|---|---|---|---|---|---|
| | | ($F_I$) Vol % | ($F_I/F_D$) | ($F_I$) Vol % | ($F_I/F_D$) |
| 1 | 1.5 | 0.92 | 0.61 | 1.46 | 0.97 |
| 2 | 1.5 | 0.96 | 0.64 | 1.20 | 0.80 |
| 3 | 1.5 | 1.00 | 0.67 | 1.20 | 0.80 |
| 4 | 1.5 | 1.20 | 0.80 | 1.45 | 0.97 |
| 5 | 1.5 | 0.89 | 0.59 | 1.20 | 0.80 |
| 6 | 1.5 | 0.95 | 0.63 | 1.35 | 0.90 |
| Mean ± SD | 1.5 ± 0.0 | 0.99 ± 0.11 | 0.66 ± 0.08 | 1.31 ± 0.13 | 0.87 ± 0.08 |

$F_I$: Inspired concentration;
$F_D$: Delivered concentration (as per vaporizer setting);
$F_I/F_D$: Concentration ratio.

Figure 14:
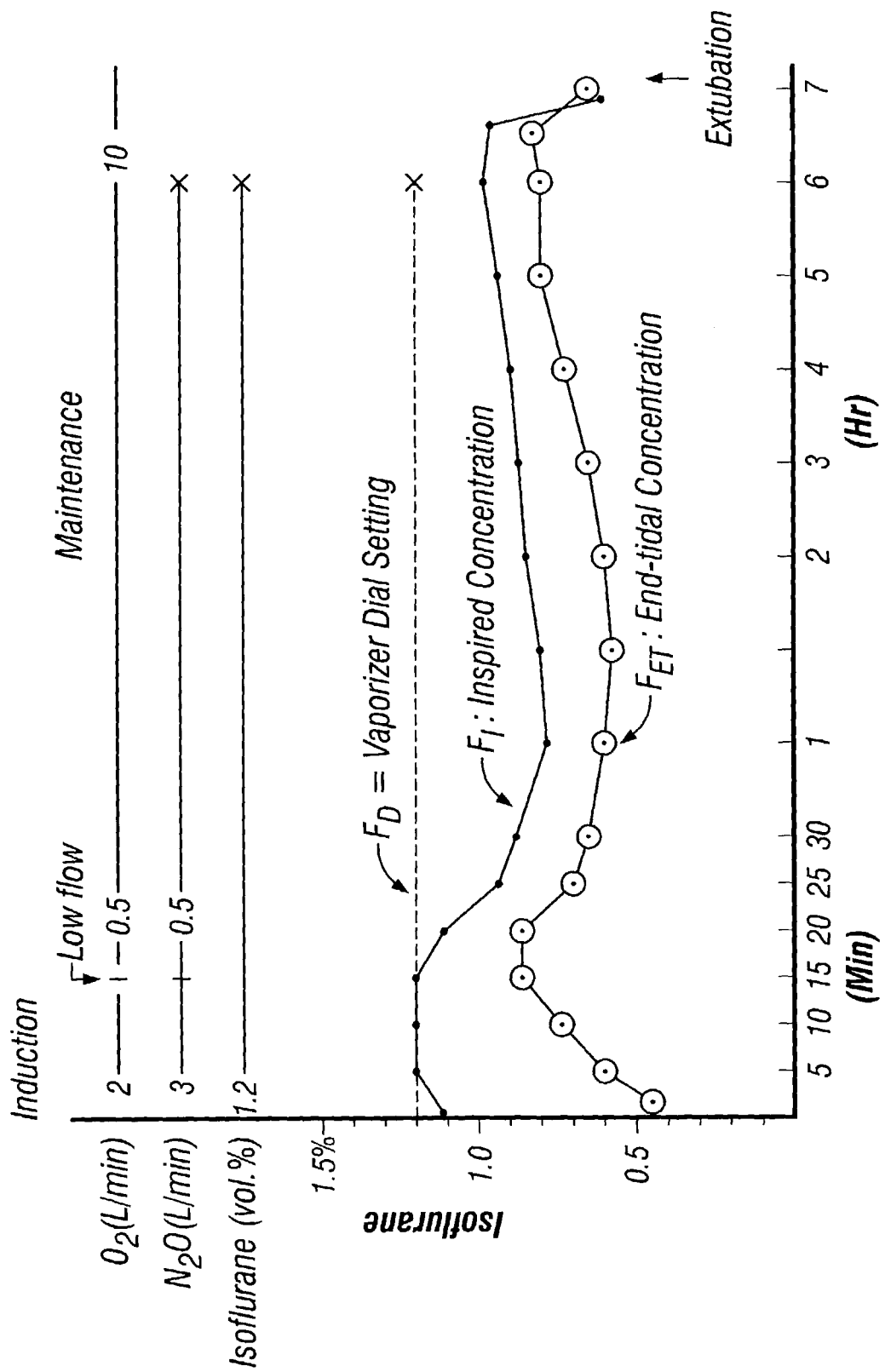
FIG. 14 is a graph illustrating the relationship of inspired ($F_I$) and end tidal ($F_D$) concentration to delivered ($F_D$) concentration with a constant vaporizer setting of 1.2% isoflurane during low flow anesthesia (1 L/min FGF).

FIG. 14 shows the changes recorded during continuous and simultaneous ring of the delivered ($F_D$), inspired ($F_I$) and end-tidal ($F_{ET}$) gas concentration low flow anesthesia of 1 L/min with a constant isoflurane vaporizer setting of 1.2% over time. Notice the significant difference between the $F_D$ gas concentration (i.e., vaporizer setting concentration) and the $F_I$ and $F_{ET}$ gas concentration.

As is now clear, the present invention provides systems and methods of providing assisted ventilation or anesthesia wherein fresh gases are provided at low flow, for example a volume of about 1 liter per minute (flows considered low range from about 0.5 to less than 3 L/min, and the $F_I/F_D$ concentration ratio can be maintained at a desired level, for example above about 0.80 or higher, by adjusting the volume of the rebreathing tube proximal of the fresh gas input. In a preferred embodiment, fresh gas flows from about 0.5 to about 3 L/min are used, and more preferably from about 1 to about 2 L/min.

Thus, exemplary embodiments and uses of the present inventions have been described. Alternative embodiments, descriptions and terms are contemplated. For example, the conduits in the circuit may be of different sizes from one another, and more than two lumens may be present. Using the present invention, larger or smaller diameter conduits may be used.

While exemplary embodiments of the present invention have been set forth above, it is to be understood that the pioneer inventions disclosed herein may be constructed or used otherwise than as specifically described.

The invention claimed is:

1. A system for providing assisted ventilation or anesthesia and that can minimize the discrepancy between the fresh gas inspired ($F_I$) and fresh gas delivered ($F_D$) concentrations and optimize utilization of fresh gases, comprising a recirculation module comprising a recirculation module fresh gas flow input, a one-way expiratory valve permitting expired gases to flow to said recirculation module from an expiratory port, and a one-way inspiratory valve permitting gas to flow to an inspiratory port from said recirculation module, wherein said recirculation module fresh gas flow input allows fresh gases to be supplied proximally of said inspiratory valve, said system further comprising a diverter valve having a diverter fresh gas flow input and at least two diverter fresh gas flow outputs, wherein said diverter valve can selectively divert all fresh gas flow either to said recirculation module fresh gas flow input or a location distal of said inspiratory valve, said diverter fresh gas outputs being formed in first and second valve lever conduits in said diverter valve, wherein said system can minimize the discrepancy between the fresh gas inspired ($F_I$) and fresh gas delivered ($F_D$) concentrations and optimize utilization of fresh gases when said diverter valve diverts all fresh gas flow to a location distal of said inspiratory valve, said recirculation module further comprising a scrubber, said scrubber comprising a patient exhaust receiving portion, a scrubbed gas output portion, and an absorbent portion located between said patient exhaust receiving portion and said scrubbed gas output portion wherein said absorbent portion can hold an absorbent composition for absorbing carbon dioxide, wherein said recirculation module fresh gas flow input is located between said absorbent portion and said one-way inspiratory valve.

2. A system for providing assisted ventilation or anesthesia and that can minimize the discrepancy between the fresh gas inspired ($F_I$) and fresh gas delivered ($F_D$) concentrations and optimize utilization of fresh gases, comprising a fresh gas flow input adapter and a fresh gas flow diverter valve, said diverter valve having a diverter valve fresh gas flow input and at least two diverter valve fresh gas flow outputs, wherein said diverter valve can divert all fresh gas flow to said fresh gas flow input adapter when said adapter is located distally of and operatively connected to an inspiratory valve of the assisted ventilation or anesthesia system when low flow anesthesia is to be provided, said system further comprising a scrubber, said scrubber comprising a patient exhaust receiving portion, a scrubbed gas output portion, and an absorbent portion located between said patient exhaust receiving portion and said scrubbed gas output portion wherein said absorbent portion can hold an absorbent composition for absorbing carbon dioxide, said scrubber having a scrubber fresh gas flow input located between said absorbent portion and said inspiratory valve, wherein said diverter valve can selectively divert all fresh gas flow to said scrubber fresh gas flow input or to said fresh gas flow input adapter, said fresh gas outputs being formed in first and second valve lever conduits in said diverter valve wherein said lever conduits do not permit gases to simultaneously flow to both of said diverter valve fresh gas outputs, wherein said system can be used to minimize the discrepancy between the fresh gas inspired ($F_I$) and fresh gas delivered ($F_D$) concentrations while providing low flow anesthesia when said diverter valve diverts all fresh gas flow to a location distal of said inspiratory valve.

3. A system for providing low flow anesthesia, comprising a fresh gas flow input adapter and a fresh gas flow diverter valve, said diverter valve having a diverter valve fresh gas flow input and at least two diverter valve fresh gas flow outputs, wherein said diverter valve can divert fresh gas flow to said fresh gas flow input adapter when said adapter is located distally of and operatively connected to an inspiratory valve of the assisted ventilation or anesthesia system, said system further comprising an expiratory valve, a breathing circuit and a recirculation module, said module isolated from said circuit by said inspiratory and expiratory valves which are operatively connected to said circuit to respectively provide inspiratory gases to and receive expiratory gases from said circuit, said module having a scrubber having an absorbing portion for holding a carbon dioxide absorbent and a fresh gas inlet portion into which fresh gases can be input to be mixed with scrubbed gases, said scrubber fresh gas inlet portion being proximal of said inspiratory valve and distal of said absorbing portion, said fresh gas flow input adapter being operatively attachable to and detachable from said circuit or module distally of said inspiratory valve to permit fresh gas flow to be provided to said circuit, wherein when said diverter valve diverts all fresh gases to said fresh gas flow input adapter the ratio of inspired anesthetic concentration to the delivered anesthetic concentration provided by said system is higher than the ratio had said fresh gas flow been provided to said scrubber fresh gas inlet portion.

4. A system for providing assisted ventilation or anesthesia and that can provide low flow anesthesia by permitting adjustment of the ratio of the fresh gas inspired ($F_I$) to fresh gas delivered ($F_D$) concentrations, comprising a first fresh gas flow input and a recirculation module, wherein expired gases may be received by said recirculation module, said recirculation module having a one-way expiratory valve permitting expired gases to flow to said recirculation module from an expiratory port, and a one-way inspiratory valve permitting gas to flow to an inspiratory port from said recirculation module, wherein said first fresh gas flow input is located distally of said inspiratory valve in an inspiratory flow path operatively connected to said inspiratory port, said system arranged so as to be capable of providing a patient fresh gases delivered via said first fresh gas flow input at low flow along with gases from said recirculation module, wherein said recirculation module comprises a scrubber having an absorbent containing portion for containing a carbon dioxide absorbent and said scrubber comprises a second fresh gas flow input, said second fresh gas flow input being located between said absorbent containing portion and said inspiratory valve so that said second fresh gas flow input is located proximally of said inspiratory valve, wherein when all fresh gas flow is input to said first fresh gas flow input distally of said inspiratory valve the ratio of inspired anesthetic concentration to the delivered anesthetic concentration provided by said system is higher than the ratio when said fresh gas flow is provided proximal to said inspiratory valve, said system further comprising lumens that form a circuit for providing and exhausting respiratory gases, wherein said lumens are formed by axially extendible and contractible conduits, wherein the volume of the respiratory gases contained in said conduits can be adjusted to maximize the inspired to delivered gas concentration ratio of said respiratory gases in low flow anesthesia when all fresh gas flow is input to said first fresh gas flow input, and further comprising a diverter valve for selectively diverting fresh gas flow to said first fresh gas flow input or to said second fresh gas flow input, said diverter valve having fresh gas outputs formed in first and second valve lever conduits in said diverter valve wherein said lever conduits do not permit gases to simultaneously flow to both of said outputs, wherein said system can be used to provide low flow anesthesia when said diverter valve diverts all fresh gas flow to said first fresh gas flow input.

5. The system of claim 4, wherein said circuit has an inspiratory lumen operatively connected to said inspiratory port to form at least part of said inspiratory flow path, said circuit further comprising an expiratory lumen operatively connected to said expiratory port, wherein said first fresh gas flow input is operatively connected to said inspiratory lumen.

6. The system of claim 4, wherein said inspiratory flow path is at least in part formed by a unilimb breathing circuit comprising a rebreathing conduit through which a patient may inhale and exhale, wherein said first fresh gas flow input is operatively connected to said rebreathing conduit.

7. The system of claim 4, further comprising a means for sealing said second fresh gas input and wherein all fresh gas flow is directed to said first fresh gas flow input.

8. The system of claim 3 or 5, wherein said circuit comprises a unilimb circuit.

* * * * *